(12) United States Patent
McCombs et al.

(10) Patent No.: US 6,663,846 B1
(45) Date of Patent: Dec. 16, 2003

(54) DEVICES AND METHODS FOR MONITORING DRUG THERAPY COMPLIANCE

(76) Inventors: Candace McCombs, 7251 Lakeview Dr. E., Mobile, AL (US) 36695; Joseph R. Lakowicz, 10037 Fox Den Rd., Ellicott City, MD (US) 21042; Omoefe Abugo, 9007-E Waltham Woods Rd., Baltimore, MD (US) 21234; Zygmunt Gryczynski, 4713 Roundhill Rd., Ellicott City, MD (US) 21043

(*) Notice: Subject to any disclaimer, the term of this patent is extended or adjusted under 35 U.S.C. 154(b) by 0 days.

(21) Appl. No.: 09/468,718

(22) Filed: Dec. 21, 1999

Related U.S. Application Data
(60) Provisional application No. 60/113,116, filed on Dec. 21, 1998.

(51) Int. Cl.$^7$ .............................................. A61K 51/00
(52) U.S. Cl. ......................................... 424/9.2; 424/9.1
(58) Field of Search .......................... 424/9.2, 9.6, 9.8, 424/9.1; 600/300, 317, 306

(56) References Cited

U.S. PATENT DOCUMENTS

| | | | | |
|---|---|---|---|---|
| 4,329,999 A | * | 5/1982 | Phillips | 128/760 |
| 4,732,153 A | * | 3/1988 | Phillips | 128/636 |
| 5,628,310 A | | 5/1997 | Rao et al. | |
| 6,068,981 A | * | 5/2000 | Rittenburg et al. | 435/7.1 |
| 6,140,137 A | * | 10/2000 | Sigler et al. | 436/536 |

FOREIGN PATENT DOCUMENTS

| EP | WO 00/14515 | 3/2000 |
|---|---|---|

OTHER PUBLICATIONS

Nair et al., "Synthesis and DNA–Binding Properties of [Ru(NH$_3$)$_4$dppz]$^{2+}$", Inorg. Chem., vol. 37: pp. 139–141 (1998).
Sacksteder et al., "Long Lived, Highly Luminescent Rhenium(I) Complexes as Molecular Probes: Intra– and Intermolecular Excited–State Interactions", J. Am. Chem. Soc., vol. 115: pp. 8230–8238 (1993).
Demas, J.N. et al., "Design and Applications of Highly Luminescent Transition Metal Complexes", Topics in Fluorescence Spectroscopy, vol. 4: Probe Design and Chemical Sensing: pp. 71–107 (1994).
Dorshow, Richard B. et al., "Noninvasive Fluorescence Detection of Hepatic and Renal Function", Journal of Biomedical Optics, vol. 3 (3): pp. 340–345 (1998).
Zhou, Jin Fu et al., "Aggregation and Degradation of Indocyanine Green", SPIE, vol. 2128: pp. 495–505 (1994).
Murphy et al., "Dipyridophenazine Complexes of Ru(II): Versatile Optical Sensors for Small and Large Molecules", SPIE vol. 2980: pp. 473–478 (1997).
Devoiselle et al., "Fluorescence Properties of Indocyanin Green—Part 1: In–Vitro Study with Micelles and Liposomes", SPIE vol. 2980: pp. 453–460 (1997).
Devoiselle et al., "Fluorescence Properties of Indocyanin Green/Part 2: In Vitro Study Related to In Vivo Behavior", SPIE vol. 2980: pp. 293–302 (1997).
Lakowicz et al., "Emerging Biomedical and Advanced Applications of Time–Resolved Fluorescence Spectroscopy", Journal of Fluorescence, vol. 4, No. 1, pp. 117–136 (1994).
Youn et al., "Fluorescence Energy Transfer Immunoassay Based on a Long–Lifetime Luminescent Metal—Ligand Complex", Analytical Biochemistry, 232, pp. 24–30 (1995).
Tolosa et al., "Optical Assay for Glucose Based on the Luminescnence Decay Time of the Long Wavelength Dye Cy5™", Published by Elsevier Sciences S.A., Sensors and Actuators B 45, pp. 93–99 (1997).
Guo et al., "Use of a Long–Lifetime Re(I) Complex in Fluorescence Polarization Immunoassays of High–Molecular–Weight Analytes", Analytical Chemistry, vol. 70, No. 3, pp. 632–637 (1998).
Lakowicz, "Emerging Applications of Fluorescence Spectroscopy to Cellular Imaging: Lifetime Imaging, Metal–Ligand Probes, Multi–Photon Excitation and Light Quenching", Scanning Microscopy Supplement 10, pp. 213–224 (1996).
Merck Manual, pp. 131–146 (1992).
Murray et al., "Medical Microbiology", The C.V. Mosby Company, pp. 219–230 (1990).
Tan, K.K., "Tuberculosis—Fighting a Losing Battle?", Singapore Med. J. 36: pp. 209–211 (1995).
Lordi, G.M. et al., "Treatment of Tuberculosis", American Family Physician, 44: pp. 219–224 (1991).
Waterhouse, R.M. et al., "Adherence to Oral Tamoxifen: A Comparison of Patient Self–Report, Pill Counts and Microelectronic Monitoring", J. Clin. Oncol., 11: pp. 1189–1197 (1993).
Cramer, J.A., "Microelectronic Systems for Monitoring and Enhancing Patient Compliance with Medication Regimens", Drugs, 49 (3): pp. 321–327 (1995).

(List continued on next page.)

*Primary Examiner*—Michael G. Hartley
(74) *Attorney, Agent, or Firm*—Kilpatrick Stockton LLP

(57) ABSTRACT

Methods and compositions for the detection and monitoring of drug therapy are provided. In particular, efficient and sensitive methods for the detection of drug ingestion are provided for determining whether individuals are complying with prescribed therapeutic regimens, and for providing a mechanism for identifying drug-resistant strains of infectious agents. The claimed methods and compositions involve the application of transdermal devices containing detection mechanisms for receiving and recording signals generated by the ingestion of a labeled drug. Such devices are attached to the skin for the duration of drug therapy and compliance is determined either by direct reading, or by remote monitoring whereby signals are transmitted from the device and received at an external site such as a healthcare facility.

10 Claims, 28 Drawing Sheets

OTHER PUBLICATIONS

Lee, J.Y. et al., "Assessing Medication Adherence by Pill Count and Electronic Monitoring in the African American Study of Kidney Disease and Hypertension (AASK) Pilot Study", Am. J. Hypertens, 9(8): pp. 719–725 (1996).

Mallion, J.M. et al., "Compliance, Electronic Monitoring and Antihypertensive Drugs", J. Hypertens. Suppl., 16(1): pp. S75–S79 (1998).

Wilson, B.C. et al., "Effect of Photosensitizer Concentration in Tissue on the Penetration Depth of Photoactivating Light", Laser Med. Sci., 1: pp. 235–244 (1986).

Lakowicz, J.R. et al., "Construction and Performance of a Variable–Frequency Phase–Modulation Fluorometer", Biophys. Chem., 21: pp. 61–78 (1985).

Lakowicz, J.R. et al., "2 GHz Frequency–Domain Fluorometer", Rev. Sci. Instrum., 57: pp. 2499–2506 (1986).

Laczko, G. et al., "A 10–GHz Frequency–Domain Fluorometer", Rev. Sci. Instrum., 61: pp. 2331–2337 (1990).

Lakowicz, J.R. et al., "Frequency–Domain Fluorescence Spectroscopy," Topics in Fluorescence Spectroscopy, vol. 1 Techniques: Plenum Press, New York, pp. 293–335 (1991).

Berndt, K. et al., "Picosecond Phase Fluorometry by Mode–Locked CW Lasers", Opt. Commun., 42: pp. 419–422 (1982).

Gratton, E. et al., "Measuring Fluorescence Decay Times by Phase–Shift and Modulation Techniques Using the High Harmonic Content of Pulsed Light Sources", Nuovo Cimento, 56B: pp. 110–124 (1980).

Gratton, E. et al., "Multifrequency Cross–Correlation Phase Fluorometer Using Synchrotron Radiation", Rev. Sci. Instrum., 55: pp. 486–494 (1984).

Nair, R.B. et al., "Optical Properties of $[Ru(phen)_2dppz]^{2+}$ as a Function of Nonaqueous Environment", Inorg. Chem., 36: pp. 962–965 (1997).

Ott, P.T. et al., "Hepatic Removal of Two Fractions of Indocyanine Green After Bolus Injection in Anesthetized Pigs", Am. J. Physiol., 266(6): pp. G1108–G1122 (1994).

Bollinger, A. et al., "Intravital Detection of Skin Capillary Aneurysms by Videomicroscopy with Indocyanine Green in Patients with Progressive Systematic Sclerosis and Related Disorders", Circulation, vol. 83 (2): pp. 546–551 (1991).

Mordon, S. et al., "Selective Laser Photocoagulation of Blood Vessels in a Hamster Skin Flap Model Using a Specific ICG Formulation", Lasers in Surg. and Med., 21: pp. 365–373 (1997).

Nakayama, M. et al., "Effects of Ephedrine on Indocyanine Green Clearance During Spinal Anesthesia: Evaluation by the Finger Piece Method", Anesth. Analg., 77: pp. 947–949 (1993).

Henschen, S. et al., "Determination of Plasma Volume and Total Blood Volume Using Indocyanine Green: A Short Review", J. Med. 24: pp. 10–27 (1993).

Schomacker, K.T. et al., "Biodistribution of Indocyanine Green in a Porcine Burn Model: Light and Fluorescence Microscopy", J. Trauma Injury, Infection, 43: pp. 813–819 (1997).

Sheridan, R.L. et al., "Burn Depth Estimation by Use of Indocyanine Green Fluorescence: Initial Human Trial", J. Burn Care Rehabil., 16(6): pp. 602–604 (1995).

Hollins, B. et al., "Fluorometric Determination of Indocyanine Green in Plasma", Clin. Chem., 33(6): pp. 765–768 (1987).

Kanda, M. et al., "Development of a Noninvasive Monitoring Instrument for Serum Indocyanine Green Dye Concentration", Appl. Optics., 31(31): pp. 6668–6675 (1992).

Mordon, S. et al., "Indocyanine Green: Physiochemical Factors Affecting its Fluorescence in vivo", Microvascular, 55: pp. 146–152 (1998).

Landsman, M.L.J. et al., "Light–absorbing Properties, Stability and Spectral Stabilization of Indocyanine Green", J. Appl. Phy., 40(4): pp. 575–583 (1976).

Van den Biesen, P.R. et al., "Yield of Fluorescence from Indocyanine Green in Plasma and Flowing Blood", Annals of Biomed. Eng., 23: pp. 475–481 (1995).

Fantini, S. et al., "Quantitative Determination of the Absorption Spectra of Chromophores in Strongly Scattering Media: a Light–Emitting Diode Based Technique", Appl. Optics, 33(22): pp. 5204–5213 (1994).

Sipior, J. et al., "Single Quantum Well Light Emitting Diodes Demonstrated as Excitation Sources for Nanosecond Phase–Modulation Fluorescence Lifetime Measurements", Rev. Scie. Instrum. 67(11): pp. 3795–3798 (1996).

Sipior, J. et al., "Blue–Light–Emitting Diode Demonstrated as an Ultraviolet Excitation Source for Nanosecond Phase-Modulation Fluorescence Lifetime Measurements", Rev. Sci. Instrum., 68(7): pp. 2666–2670 (1997).

Sacksteder et al., "Long–Lived, Highly Luminescent Rhenium (I) Complexes as Molecular Probes: Intra– and Intermolecular Excited–State Interactions", J. Am. Chem. Soc., 15 (18): pp. 8230–8238 (1993).

Abugo et al., "Modulation Sensing of Fluorophores in Tissue: A New Approach to Drug Compliance Monitoring", J. Biomed. Opt., vol. 4, pp. 429–442 (1999).

Abugo et al., "Preliminary Studies on the Use of Modulation Sensing for Non–Invasive Monitoring of Drug Compliance", Proc. Spie–Int. Soc. Opt. Eng.", (3602 –Advances in Fluoroescence Sensing Technology IV), pp. 297–308 (1999).

Database WPI, Section Ch, Week 199849, Derwent Publications Ltd., London, GB; Class B04, AN 1998–572114 (XP002144142) and JP 10 253622 A (Nippon Sharing KK), Sep. 25, 1998 (abstract).

Gryczynski et al., "A New Front–Face Optical Cell for Measuring Weak Fluorescent Emissions With Time Resolution in the Picosecond Time Scale", Biophysical Chemistry, vol. 48, pp. 31–38 (1993).

Gryczynski et al., "Polarization Sensing of Fluorophores in Tissues for Drug Compliance Monitoring", Analytical Biochemistry, vol. 273, pp. 204–211 (1999).

International Search Report in related PCT/US99/30508 dated Sep. 19, 2000.

* cited by examiner

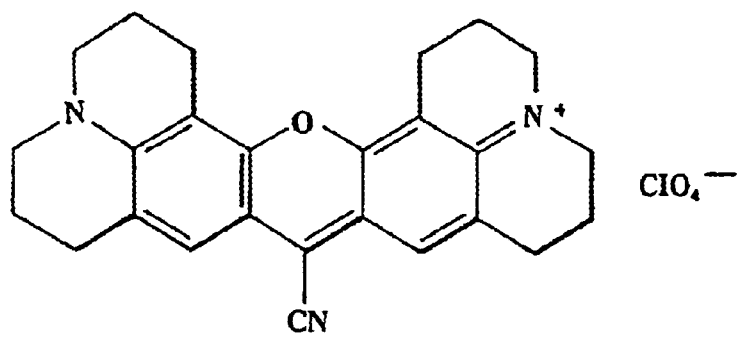
Rh 800
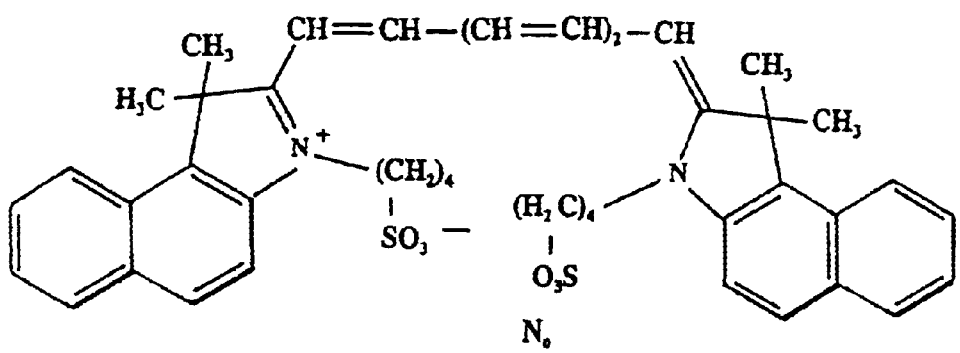
IcG
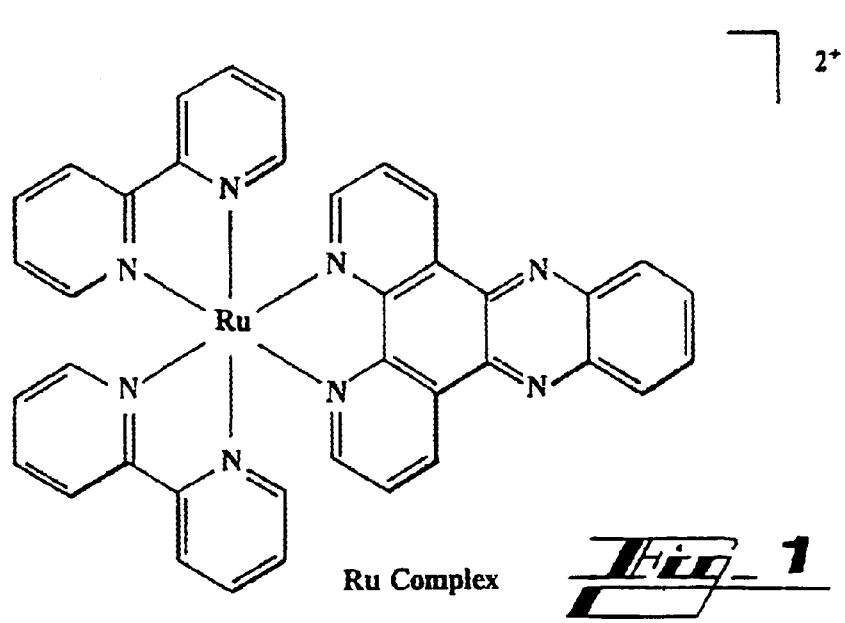
Ru Complex

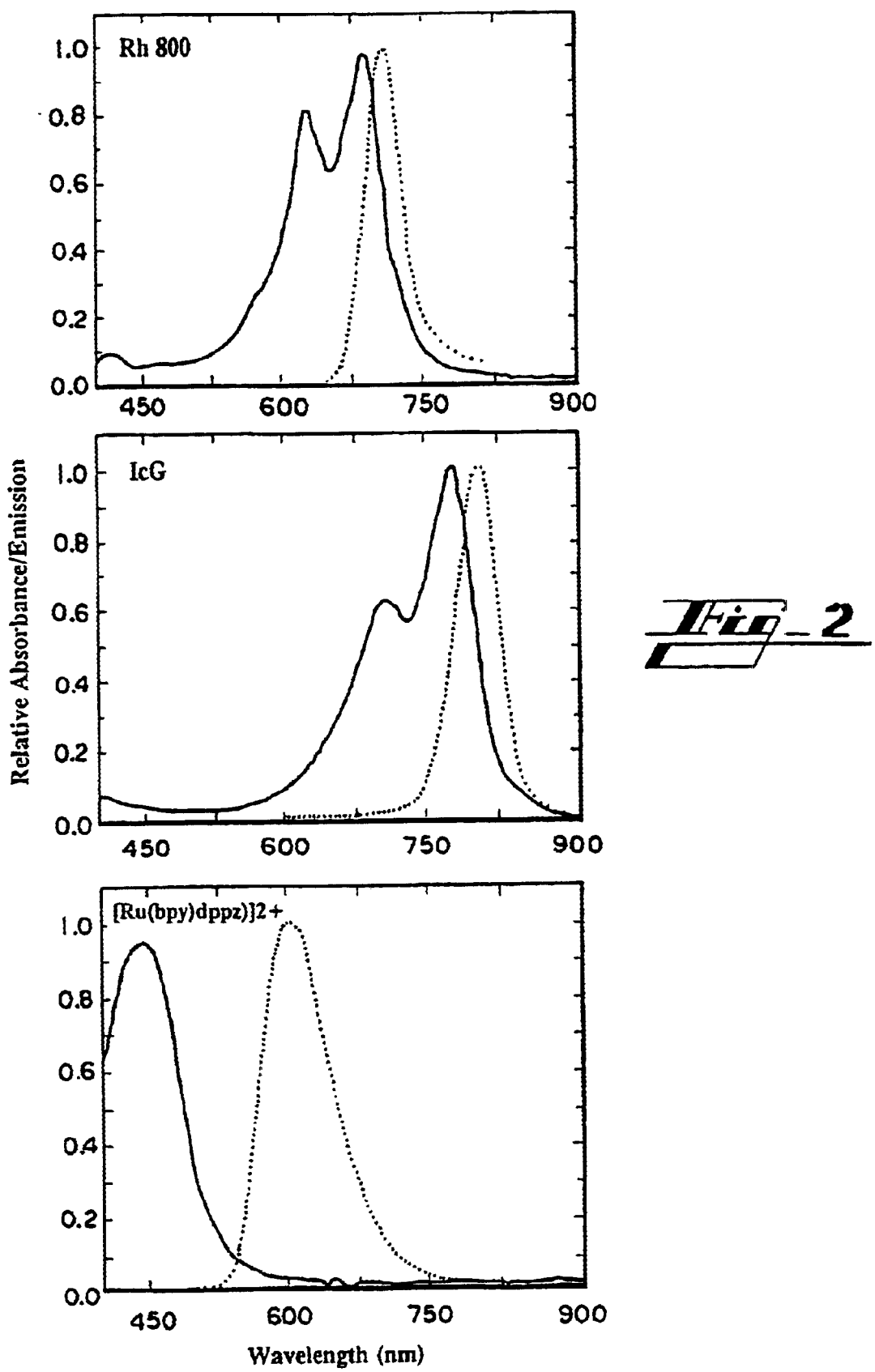
Fig_2

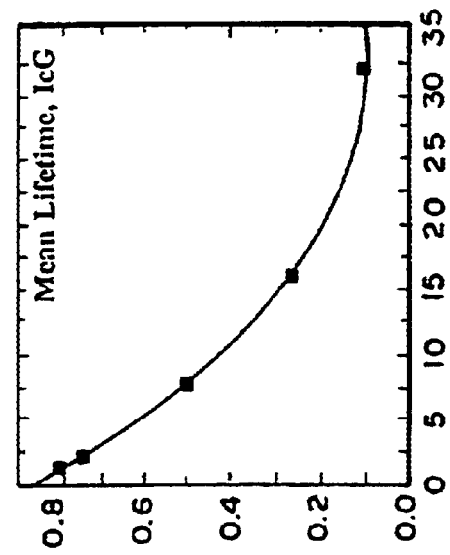
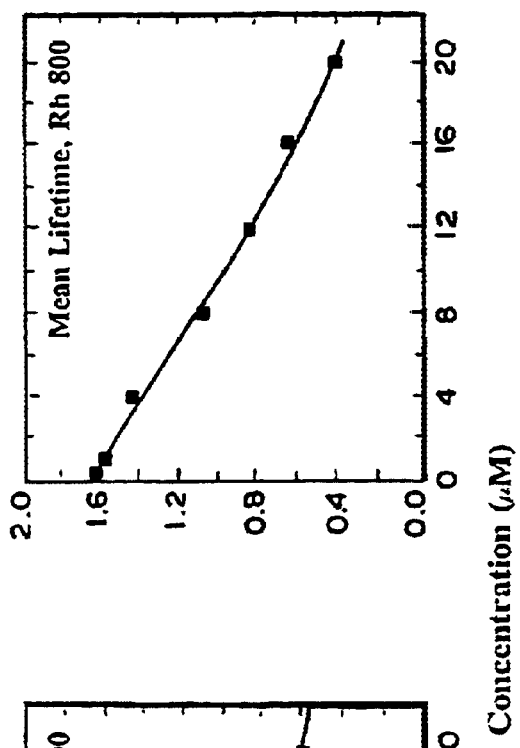
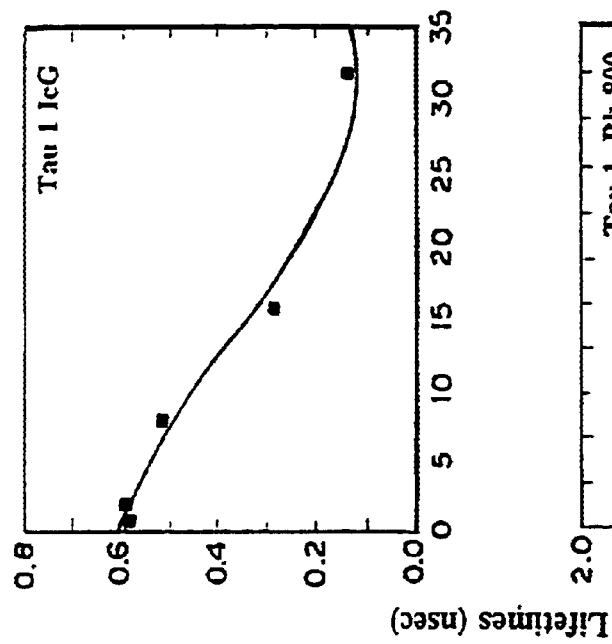
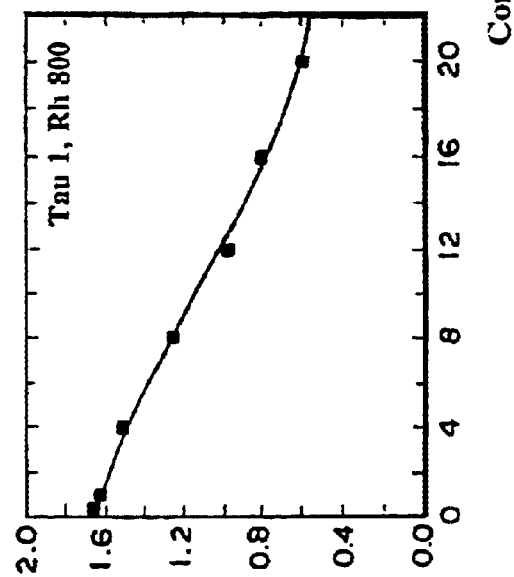
Fig. 6

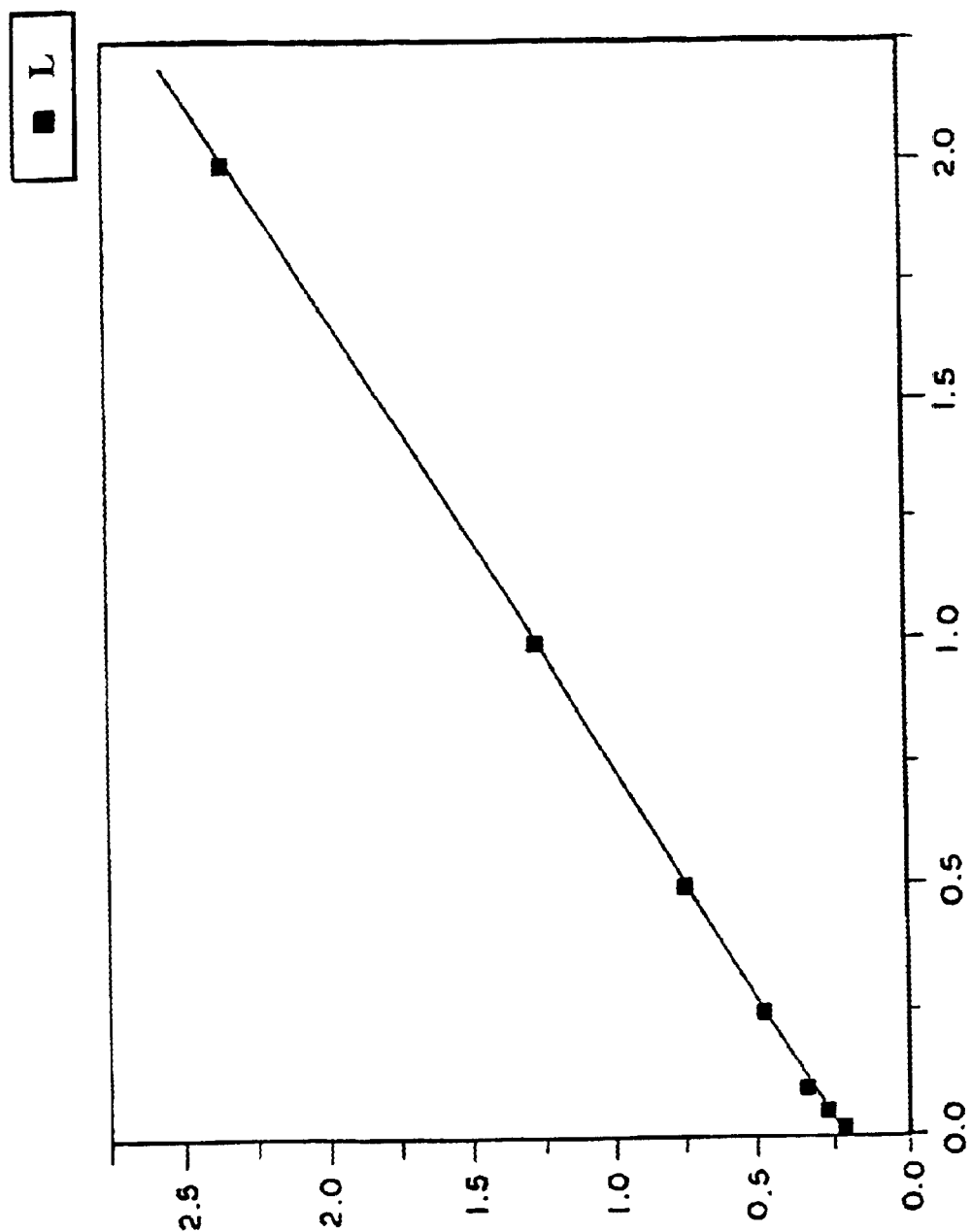
Fig_9A

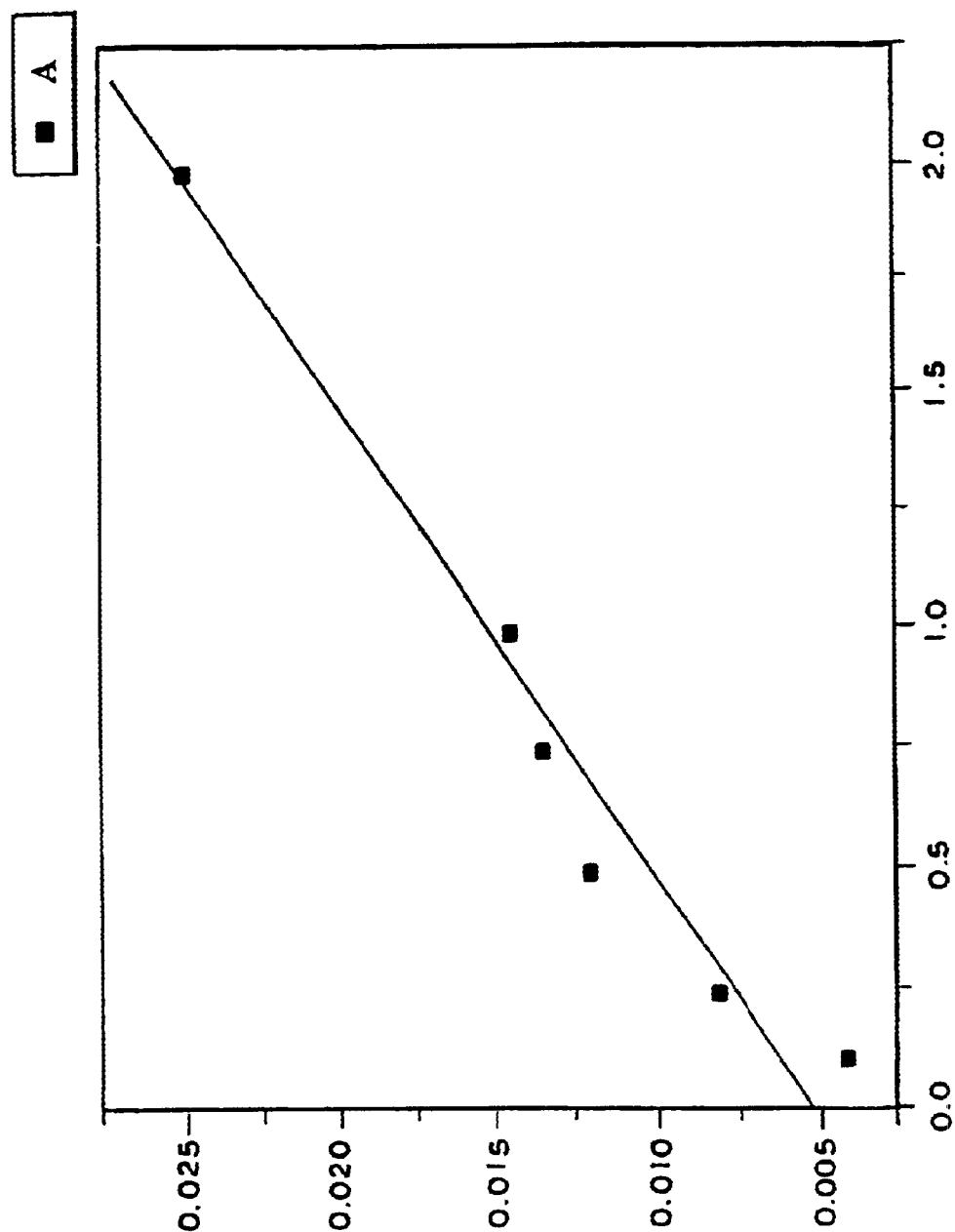
Fig_9B

Fig_11

Fig_13

Fig_14

Fig_17

Fig_18

Table 1. Lifetime of Ruthenium bis-2,2'-bipyridine dipyridophenazine in polyvinyl alcohol film

| $T_1$ (μs) | $T_2$ (μs) | $a_1{}^a$ | $f_1{}^b$ | $\overline{T}$ (μs)$^c$ |
|---|---|---|---|---|
| 1.207 | 0.405 | 0.280 | 0.535 | 0.834 |

$^a a_1 + a_2 = 1.0.$ $^b f_1 + f_2 = 1.0.$ $^c T = \sum a_i T_i^2 / \sum a_i T_i$

FIG. 20

Table II. Rhodamine 800 lifetimes in aqueous and 0.5% intralipid solutions

| Media | Rh800(μM) | $T_1$ (ns) | $T_2$ (ns) | $a_1$ | $f_1$ | $T$ (ns) |
|---|---|---|---|---|---|---|
| Water | 1.0-10.0 | 0.686 | | 1.000 | 1.000 | 0.686 |
| 0.5% Intralipid | 0.3 | 1.650 | 0.351 | 0.892 | 0.975 | 1.618 |
| | 1.0 | 1.633 | 0.583 | 0.849 | 0.940 | 1.571 |
| | 4.0 | 1.511 | 0.487 | 0.810 | 0.930 | 1.439 |
| | 8.0 | 1.263 | 0.432 | 0.538 | 0.773 | 1.074 |
| | 12.0 | 0.982 | 0.316 | 0.522 | 0.772 | 0.830 |
| | 16.0 | 0.791 | 0.227 | 0.419 | 0.715 | 0.631 |
| | 20.0 | 0.582 | 0.173 | 0.265 | 0.547 | 0.397 |

Fig. 21

Table III

Indocyanine green lifetimes in aqueous and 0.5% intralipid solutions

| Media | ICG(μM) | $T_1$ (ns) | $T_2$ (ns) | $a_1$ | $f_1$ | $\bar{T}$ (ns) |
|---|---|---|---|---|---|---|
| Water | 7.0 | 0.430 | 0.071 | 0.494 | 0.855 | 0.378 |
| 0.5% | 1.0 | 0.581 | 4.195 | 0.991 | 0.948 | 0.798 |
| Intralipid | 2.0 | 0.584 | 4.502 | 0.995 | 0.960 | 0.739 |
|  | 8.0 | 0.513 | 0.093 | 0.812 | 0.959 | 0.496 |
|  | 16.0 | 0.286 | 0.042 | 0.514 | 0.879 | 0.256 |
|  | 32.0 | 0.131 | 2e-4 | 0.010 | 0.788 | 0.103 |

FIG. 22

Table IV  Global intensity decay analysis of Rh800 in 0.5% intralipid with the Ru-complex PVA film.[a]

| Rh800 (μM) | $T_L$ (ns)[b] | $T_{S1}$ (ns)[c] | $T_{S2}$ (ns) | $a_s$[d] | $f_s$[e] | $T_m$ (ns) |
|---|---|---|---|---|---|---|
| 0.05 | 545.08 | 1.616 | 1.212 | 0.988 | 0.184 | 444.55 |
| 0.10 |  |  |  | 0.993 | 0.300 | 380.90 |
| 0.25 |  |  |  | 0.998 | 0.534 | 254.78 |
| 0.50 |  |  |  | 0.999 | 0.681 | 173.34 |
| 1.00 |  |  |  | 0.999 | 0.803 | 108.56 |
| 2.00 |  |  |  | 0.999 | 0.856 | 80.00 |

[a] For the global intensity decay analysis, lifetimes were held constant at all dye concentrations.
[b] $T_L$ = long lifetime.
[c] $L_{S1}$ = short lifetime.
[d] $a_L + a_s = 1.0$, where $a_s = a_{s1} + a_{s2}$
[e] $f_L + f_s = 1.0$, where $f_s = f_{s1} + f_{s2}$

Fig. 23

Table V. Global intensity decay analysis of IcG in 0.5% intralipid with the Ru-complex reference

| IcG (μM) | $T_L$ (ns) | $T_{S1}$ (ns) | $T_{S2}$ (ns) | $a_s$ | $f_s$ | $\overline{T}_m$ (ns) |
|---|---|---|---|---|---|---|
| 0.25 | 584.26 | 1.494 | 0.428 | 0.993 | 0.130 | 508.44 |
| 0.50 | | | | 0.996 | 0.200 | 467.33 |
| 1.00 | | | | 0.997 | 0.299 | 409.69 |
| 2.00 | | | | 0.998 | 0.437 | 329.44 |
| 4.00 | | | | 0.999 | 0.537 | 270.91 |
| 6.00 | | | | 0.999 | 0.572 | 250.21 |
| 10.00 | | | | 0.999 | 0.601 | 233.26 |
| 20.00 | | | | 0.999 | 0.659 | 199.70 |
| 40.00 | | | | 0.999 | 0.719 | 164.38 |

Fig. 24

Table VI  Global intensity decay analysis of IcG in chicken muscle with the Ru-complex reference

| IcG(μM) | $T_L$ (ns) | $T_{S1}$ (ns) | $T_{S2}$ (ns) | $a_s$ | $f_s$ | $\bar{T}_m$ (ns) |
|---|---|---|---|---|---|---|
| 1.00 | 348.20 | 4.084 | 0.884 | 0.989 | 0.261 | 257.96 |
| 5.00 | | | | 0.991 | 0.328 | 234.84 |
| 10.0 | | | | 0.994 | 0.411 | 206.06 |
| 20.0 | | | | 0.997 | 0.517 | 169.36 |

Fig. 25

Table VII  Global intensity decay analysis of Rh800 in chicken muscle with the Ru-complex reference

| Rh800(μM) | $T_L$ (ns) | $T_{S1}$ (ns) | $T_{S2}$ (ns) | $a_s$ | $f_s$ | $\bar{T}$ (ns) |
|---|---|---|---|---|---|---|
| 1.00 | 502 | 1.748 | 0.485 | 0.997 | 0.391 | 306 |
| 2.00 | | | | 0.997 | 0.518 | 242 |
| 5.00 | | | | 0.999 | 0.738 | 132 |
| 10.0 | | | | 0.999 | 0.865 | 69 |

Fig. 26

DEVICES AND METHODS FOR MONITORING DRUG THERAPY COMPLIANCE

CROSS REFERENCE TO RELATED PATENT APPLICATION

This application is a non-provisional of application of U.S. Provisional Application Serial No. 60/113,116 filed Dec. 21, 1998.

FIELD OF INVENTION

The present invention relates to methods and compositions for monitoring devices useful for determining whether patients have complied with prescribed therapeutic regimens. In particular, the detection devices of the present invention comprise instruments that may be placed on a patient's skin for transdermal detection of a signal, such as a fluorescent signal, for indicating positive or negative compliance.

BACKGROUND OF THE INVENTION

Nonadherence to therapy has been cited as one of the greatest obstacles to the elimination of certain infectious diseases such as tuberculosis (TB). Nonadherence results in treatment failure, relapse, continued infectiousness, and is one of the principal "drivers" for the emergence of drug-resistant strains of infectious agents.

Although numerous systems and procedures have been suggested and implemented in an attempt to improve drug therapy compliance, there remains a need for a system that is easily administered and simple to use. For example, "Directly Observed Treatment Short-Course" (DOTS), in which the ingestion of every dose of prescribed drugs is witnessed by a health care worker or other responsible individual, has been hailed by the World Health Organization (WHO) as the "breakthrough of the century" because of its potential to ensure compliance. There are shortcomings to DOTS, however, including high cost, limited availability, patient resentment, and the requirement for a high degree of patient cooperation. Patients must faithfully attend a clinic or rendezvous with healthcare workers. Recent surveys of programs based on directly observed therapy indicate that they experience an average noncompliance rate of 18%. When patients fail to cooperate with directly observed therapy, involuntary incarceration is the final resort of health officials. Furthermore, each of the listed shortcomings are even more exaggerated in the developing world, where severe shortages in resources such as basic healthcare presents tremendous opportunity for the breeding and development of more drug-resistant and virulent strains of infectious agents. [1–3] In summary, although a variety of methods have been proposed to monitor compliance, including pill counting, microelectronic event monitoring system (MEMS) and other approaches [4–6], as of yet there is no easily administered system that ensures therapeutic compliance effectively and economically.

As valuable as directly observed therapy has proven to be, it requires the participation of several individuals and multiple procedures which in many cases makes therapy burdensome, resulting in ultimate non-compliance. Patients, physicians, and public health officials agree that more efficient ways to assure compliance are needed.

Recent scientific reporting has documented an alarming rise in infectious disease. Some diseases that were previously considered to be "under control" have re-emerged, many of them carried by drug-resistant strains making routine and standard therapeutic intervention useless. For example, it is well known that human infections caused by mycobacteria have been widespread since ancient times and that tuberculosis was a leading cause of death less than 250 years ago. What is less well known, however, is that mycobacterial diseases still constitute a leading cause of morbidity and mortality in countries with limited medical resources and can cause overwhelming, disseminated disease in immunocompromised patients. In fact, the number of reported tuberculosis cases has also been increasing in the developed world. What is even more troubling is that numerous drug-resistant mycobacterial strains have been identified.

Tuberculosis

Tuberculosis has been a major disease of mankind for most of recorded history. The incidence of the disease declined in parallel with advancing standards of living since at least the mid-nineteenth century. However, in spite of the efforts of numerous health organizations worldwide, the eradication of tuberculosis (TB) has never been achieved, nor is eradication imminent. Nearly half of the world's population is infected with *M. tuberculosis,* with approximately 8 million new cases and 3 million deaths attributable to TB yearly.

After decades of decline, TB is on the rise. In the United States, up to 10 million individuals are believed to be infected. Almost 28,000 new cases were reported in 1990, a 9.4 percent increase over 1989. A sixteen percent increase was observed from 1985 to 1990. TB is acquired by the respiratory route when actively infected individuals spread this infection efficiently by coughing or sneezing "droplet nuclei" which contain viable bacilli. Overcrowded living conditions and shared air spaces are especially conducive to the spread of TB, underlying the increase in instances that have been observed in the U.S. in prison inmates and among the homeless in larger cities.

Alarmingly, outbreaks of TB cases resistant to at least two of the most effective anti-TB drugs rifampin (RFP) and isoniazide (INH) are being reported in hospitals and correctional facilities with evidence of transmission to human immunodeficiency virus (HIV) negative individuals. Approximately half the patients with acquired immune deficiency syndrome (AIDS) will acquire a mycobacterial infection, with TB being an especially devastating complication. AIDS patients are at higher risks of developing clinical TB and anti-TB treatment seems to be less effective. Consequently, the infection often progresses to a fatal disseminated disease.

The World Health Organization (WHO) continues to encourage the battle against TB, recommending prevention initiatives such as the "Expanded Program on Immunization" (EPI), and as mentioned above, therapeutic compliance initiatives such as "Directly Observed Treatment Short-Course" (DOTS). For the eradication of TB, diagnosis, treatment, and prevention are equally important. Rapid detection of active TB patients will lead to early treatment by which about 90% cure is expected. Therefore, early diagnosis is critical for the battle against TB. Therapeutic compliance will ensure not only elimination of infection, but also reduction in the emergence of drug-resistance strains.

The emergence of drug-resistant *M. tuberculosis* is an extremely disturbing phenomenon. The rate of new TB cases proven resistant to at least one standard drug increased from 10 percent in the early 1980's to 23 percent in 1991. Currently, seven percent of all cases of TB are resistant to at least one drug, over double the number from the early 1980.

Compliance with therapeutic regimens, therefore, is a crucial component in efforts to eliminate TB and prevent the emergence of drug-resistant strains.

Although over 37 species of mycobacteria have been identified, more than 95% of all human infections are caused by six species of mycobacteria: *M. tuberculosis, M. avium-intracellulare, M. kansasii, M. frotuitum, M. chelonae,* and *M. leprae.* In addition, infections resulting from drug-resistant strains have also been observed.

The most prevalent mycobacterial disease in humans is tuberculosis (TB) which is caused by *M. tuberculosis, M. bovis,* or *M. africanum* (Merck Manual 1992). Infection is typically initiated by the inhalation of infectious particles which are able to reach the terminal pathways. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately destructed. The disease is further disseminated during the initial stages by the infected macrophages which travel to local lymph nodes, as well as into the blood stream and other tissues such as the bone marrow, spleen, kidneys, bone and central nervous system. (See Murray et al. *Medical Microbiology*, The C.V. Mosby Company 219–230 (1990)).

Additionally, mycobacteria other than *M. tuberculosis* are also becoming increasingly problematic as elements in the list of opportunistic infections that plague the AIDS patient. Organisms from the *Avium-intracellulare* complex (MAC), especially serotypes four and eight, account for 68% of the mycobacterial isolates from AIDS patients. Enormous numbers of MAC are found (up to $10^{10}$ acid-fast bacilli per gram of tissue) and, consequently the prognosis for the infected AIDS patient is poor.

Mycobacteria, including *Mycobacterium avium,* are intracellular parasites that are capable of growth within the host in cells such as macrophages. The mycobacteria grow slowly, produce no endotoxin and are not motile. They multiply within the macrophages, kill the macrophage and are taken up by new macrophages to start the process over. Host resistance depends upon activation of the macrophages. Activated macrophages are able to kill the bacteria that reside within the cell. This activation depends upon specific T-cells which are produced as the result of a cell-mediated immune reaction against proteins of the mycobacteria. Mycobacterial infections have been likened to a war of attrition in which there is a delicate balance between the ability of the mycobacteria to survive within the macrophages and the ability of the host to activate macrophages sufficiently to kill them. In the absence of rapidly acting anti-infective compounds, the goal of therapy is to tip the balance in favor of the host.

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

*Mycobacterium avium* bacilli occur in several distinct colony forms. Bacilli which grow as transparent or rough colonies on conventional laboratory media are able to multiply within macrophages in tissue culture, are virulent when injected into susceptible mice, and are resistant to antibiotics. Rough or transparent bacilli which are maintained on laboratory culture media often spontaneously assume an opaque colony morphology at which time they fail to grow in macrophages, are avirulent in mice, and are highly susceptible to antibiotics. The differences in colony morphology between the transparent, rough and opaque strains of *Mycobacterium avium* are almost certainly due to the presence of a glycolipid coating on the surface of transparent and rough organisms which acts as a protective capsule. This capsule, or coating, is composed primarily of C-mycosides which apparently shield the virulent *Mycobacterium avium* organisms from lysosomal enzymes and antibiotics. By contrast, the non-virulent opaque forms of *Mycobacterium avium* have very little C-mycoside on their surface. Both resistance to antibiotics and resistance to killing by macrophages have been attributed to the glycolipid barrier on the surface of *Mycobacterium avium.*

Diagnosis of TB is confirmed by the isolation and identification of the pathogen, although conventional diagnosis is based on sputum smears, chest X-ray examination (CXR), and clinical symptoms. Isolation of the mycobacteria on a medium takes as long a time as six to eight weeks. Species identification takes a further two weeks. There are several other techniques for detecting mycobacteria rapidly such as the polymerase chain reaction (PCR), mycobacterium tuberculosis direct test, or amplified mycobacterium tuberculosis direct test (MTD), and detection assays that utilize radioactive labels (2–5).

One diagnostic test that is widely used is the tuberculin skin test. Although numerous versions of the skin test are available, typically two preparations of tuberculin antigens are used: old tuberculin and purified protein derivative (PPD). The antigen is either injected into the skin intradermally, or is topically applied and then transdermally transported into the skin with the use of a multiprong inoculator (Tine test). Although developments have been made in the area of diagnosis and prevention of TB, there is still a need for improved methods for ensuring drug therapy compliance by infected individuals. Compliance is important not only effective for treatment and elimination of infection, it is also important for preventing the development of drug-resistant strains.

What is needed are inexpensive and accurate methods and compositions for determining whether patients have complied with prescribed therapeutic regimens. The methods and compositions should be simple and easily administered, and require minimum supervision. Preferably the detection system should not require involved analysis, such as chemical analysis of bodily fluids, rather, it should be a sensing device that monitors signals non-invasively. Additionally what is needed is a monitoring system for children who are often under the care of several adults making monitoring of therapeutic compliance both complicated and prone to errors such as duplicative administration of medication.

A compliance system that does not require the invasion of the skin surface of the tested person would minimize the exposure of the health care professional administering the test to the bodily fluids of the tested person and lessen the risk of transmission of other infectious agents that may be present in the tested person. A system that is easily implemented and has an easily determined positive or negative outcome is essential when monitoring compliance with a therapeutic regimen for highly infectious diseases such as tuberculosis, in individuals ranging from homeless persons and prison inmates, to schoolchildren and senior citizens.

SUMMARY OF THE INVENTION

Efficient and sensitive methods and compositions for the detection of compliance with therapeutic regimens are provided. In accordance with a preferred embodiment of the present invention, transdermal devices containing detection mechanisms are provided. Such transdermal devices are worn on the skin to detect ingestion of a drug and a signal is periodically generated to report whether or not the wearer has taken the drug. The signal may then be transmitted to a "reminder center" at a central location such as a public health facility, so that the patient can be prompted to take his medication if non-compliance is detected.

Unlike prior art detection methods, the detection methods provided herein are highly sensitive, easily administered and non-invasive. Most importantly, the detection methods are especially effective in transdermal detection of fluorescent signals, thereby eliminating the need for involved chemical analysis of bodily fluids, supervision by healthcare workers, or use of dangerous tracer substances such as radioactive labels.

The detection methods and compositions described herein comprise the incorporation of a detector, such as a fluorescent dye, in a drug, so that the detector can be monitored by a device comprising a transdermal instrument.

The detection methods and compositions described herein may optionally comprise features that enable filtration of interfering signals, data processing, data storage, timing devices, methods for signaling a patient to take medication, display panels and data recovery system. In addition, the detection methods and compositions described herein may further comprise a programming feature enabling the user to program drug schedules for prescribed medications. Importantly, the devices of the present invention may also comprise a security or tamper-proof feature that prevents unauthorized use of the device such as modification of settings, data input, or data analysis.

Accordingly, it is an object of the present invention to provide sensitive detection methods and compositions for monitoring compliance with therapeutic regimens.

It is another object of the present invention to provide sensitive detection methods and compositions that can be used transdermally.

It is yet another object of the present invention to provide sensitive detection methods and compositions for determining compliance with therapeutic regimens in order to remind patients to take their medication.

It is another object of the present invention to provide sensitive detection methods and compositions for creating a database of therapeutic compliance and emergence of drug-resistant infectious agents.

Yet another object of the present invention is to provide a kit for sensitive detection methods and compositions for monitoring therapeutic compliance.

It is another object of the present invention to provide sensitive detection methods and compositions for the monitoring of the clinical status of patients following therapy.

Another object of the present invention is to provide compositions and methods useful for monitoring therapeutic compliance in a variety of diseases and disorders, including, but not limited to infectious diseases, immunodeficiency diseases, cardiovascular disorders, pulmonary disorders, gastrointestinal, hepatic and biliary disorders, endocrine disorders, cancer, musculoskeletal and connective tissue disorders, neurologic and psychiatric disorders, genitourinary disorders and other physiological disorders and diseases.

Yet another object of the present invention is to provide compositions and methods useful for monitoring therapeutic compliance for therapeutic compositions comprising antimicrobial agents, antibiotics, antivirals, antidepressants, β-lactam antibiotics, aminoglycosides, macrolides, lincomycin, clindamycin, tetracyclines, quinolones, polypeptides, sulfonamides, trimethoprims, sulfamethoxazoles, growth factors, lipids, neurotransmitters, vitamins, and minerals.

Another object of the present invention is to provide compositions and methods useful for monitoring therapeutic compliance for individuals participating in clinical trials and the like.

It is yet another object of the present invention to provide compositions and methods useful for monitoring therapeutic compliance in patients discretely and without revealing the patients' illness.

Yet another object of the present invention to provide compositions and methods useful for monitoring therapeutic compliance in patients wherein the compliance device is capable of blanking and registration.

A further object of the present invention to provide compositions and methods useful for monitoring therapeutic compliance in patients in order to improve physician patient communication.

These and other objects, features and advantages of the present invention will become apparent after a review of the following detailed description of the disclosed embodiments and the appended claims.

BRIEF DESCRIPTION OF THE FIGURES

FIG. 1 is a schematic representation of the structures of Rhodamine 800, Indocyanine Green and Ruthenium bis-2, 2'-bipyridine dipyridophenazine, [Ru(bpy)(dppz)]$^{2+}$.

FIG. 2 provides graphs showing the relative absorbance (–) and emission spectra of rhodamine 800, indocyanine green and ruthenium bis-2,2'-bipyridine dipyridophenazine complex, [Ru(bpy)(dppz)]$^{2+}$.

FIG. 6 provides graphs showing dependence of the decay times and mean decay times of Rh800 and IcG in 0.5% intralipid.

FIG. 9A provides a graph showing the dependence of the fractional intensity of the short component ($f_s'$) and the unnormalized intensity ($f_s'$) on the concentration of Rh800.

FIG. 9B provides a graph showing emission spectra of Rh800.

FIG. 20 provide Table 1 wherein lifetime and intensity decay time of ruthenium bis-2,2'-bipyridine dipyridophenazine in polyvinyl film is provided.

FIG. 21 provides Table 11 showing rhodamine 800 lifetimes in aqueous and 0.5% intralipid solutions. The data is shown as analyzed in terms of the multiexponential model.

FIG. 22 provides Table III showing indocyanine green lifetimes in aqueous and 0.5% intralipid solutions. The results demonstrate that decay times and mean decay time decreases with increases in IcG concentration (Table III as shown in FIG. 22).

FIG. 23 provides Table IV showing global intensity decay analysis of Rh800 in 0.5% intralipid with the Ru-complex PVA film.

FIG. 24 provides Table V showing global intensity decay analysis of IcG in 0.5% intralipid with the Ru-complex reference.

FIG. 25 provides Table VI showing global intensity decay analysis of IcG in chicken muscle with the Ru-complex reference.

Table VI provides data demonstrating the ability to detect the indocyanine green in chicken muscle through chicken skin as demonstrated by lifetime measurements. This table lists the lifetimes and factional intensities recovered from the multi-exponential analysis. The decay times are those expected for the Ru complex and for indocyanine green demonstrating that both fluorophores will resolve in the measurement.

FIG. 26 provides Table VII showing global intensity decay analysis of Rh800 in chicken muscle with the Ru-complex reference.

Figure 27:
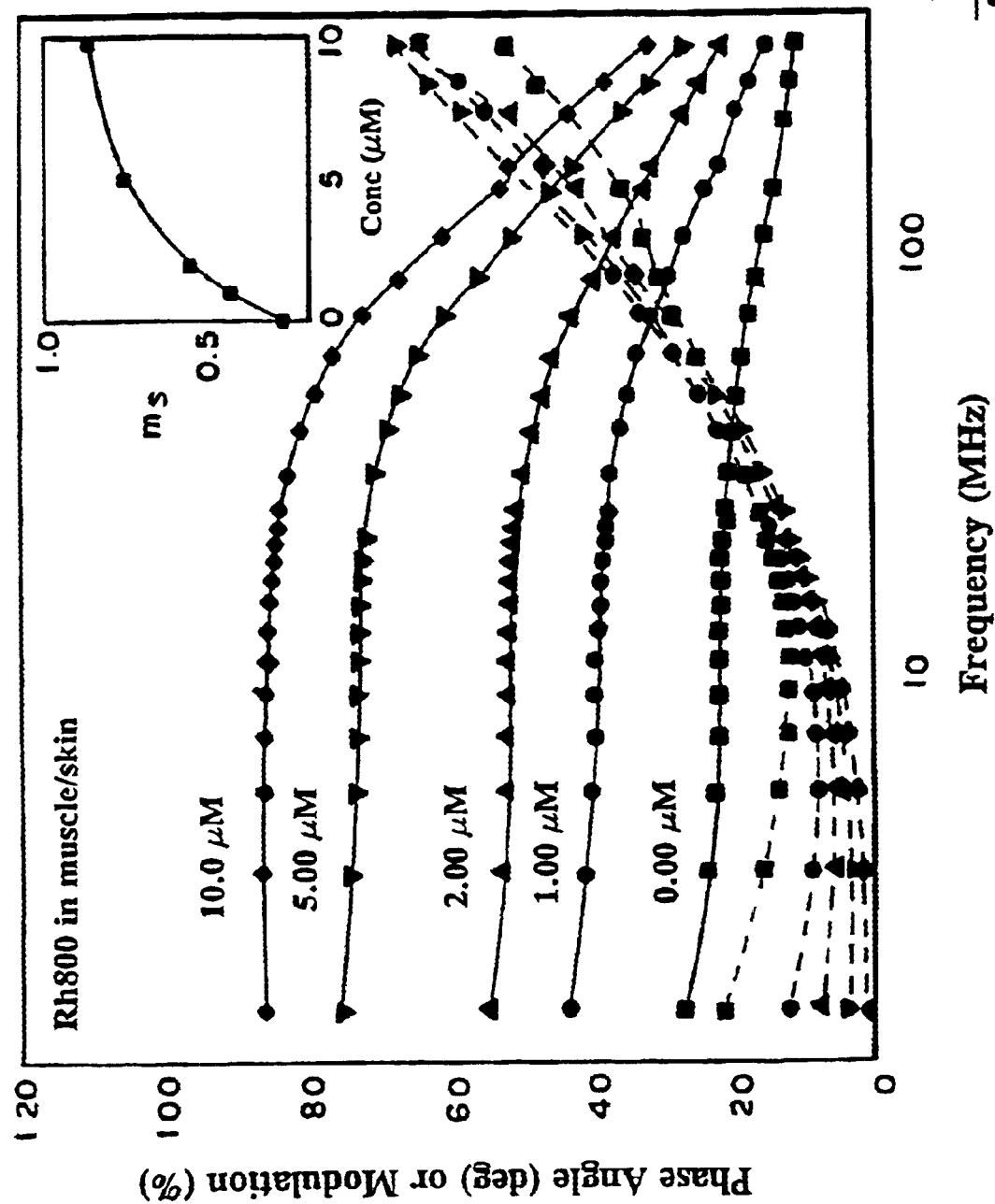

FIG. 27 provides a graph showing phase angle/modulation of Rh800 in muscle/skin over varying concentrations.

DETAILED DESCRIPTION

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference.

Nonadherence to therapeutic regimens has been recognized as a serious threat against the elimination of infectious diseases such as tuberculosis (TB). Not only does a patient suffer from failing to comply with his prescribed therapy, nonadherence gives rise to other complications such as relapse, continued infectiousness, and is one of the principal causes for the emergence of drug-resistant strains of infectious agents.

Although programs and initiatives such as directly observed therapy have proven to be valuable, they are often inefficient because they require the involvement of cumbersome procedures which in many cases make therapy burdensome, resulting in ultimate non-compliance.

In addition, the emergence of dangerous drug-resistant strains of infectious agents has further heightened the need for ensuring that infected patients comply with prescribed therapy.

Many people who suffer from disease caused by infectious agents such as mycobacteria, are poor, or live in areas with inadequate access to health care facilities. Such people are not easily monitored for compliance, and inexpensive and noninvasive methods for determining compliance are necessary.

The present invention provides for monitoring devices comprising detection mechanisms for determining whether a patient has complied with his prescribed drug therapy. In addition to satisfying a compelling public health need to assure compliance with drug therapy, the remotely monitored therapy device/systems of the present invention also function suprisingly well for other applications. For example, other medical situations where prolonged therapy makes compliance difficult, or where nonadherence drives the emergence of drug-resistant strains include the use of antibiotics, including antifungals, immunosuppressive therapy following organ transplantation, and AIDS therapy. In addition, in order to best interpret clinical trial results, pharmaceutical companies may measure compliance by the methods of the present invention.

The present invention provides for a transdermal sensor that, with minimal effort on the part of the patient, accurately detects that a therapeutic drug dose has been ingested. The device may optionally transmit this information to a remote monitoring facility, providing an accurate, real-time record of when each drug dose was ingested. The system is resistant to tampering thereby ensuring accurate detection of compliance.

In addition to the drug sensing component, the methods and compositions of the present invention comprise a total of up to four key elements to constitute a remote monitoring device/system: a fluorescent tracer, detection device, signal transmission system and a signal receiving system.

The detection methods and compositions described herein may optionally comprise features that enable filtration of interfering signals, data processing, data storage, timing devices, methods for signaling a patient to take medication, display panels and data recovery system. In addition, the detection methods and compositions described herein may further comprise a programming feature enabling the user to program drug schedules for prescribed medications. Importantly, the devices of the present invention may also comprise a security or tamper-proof feature that prevents unauthorized use of the device such as modification of settings, data input, or data analysis.

Fluorescent Tracer

The devices of the present invention detect a fluorescent tracer that is incorporated into, or coated onto, the drug tablet. Thus any current or future drug, or drug combination tablet, could be modified to be detectable by the methods and compositions of the present invention. There are presently several fluorescent compounds that are FDA approved for human use, including but not limited to, fluorescein, indocyanin green and rhodamine B. The tracer compounds used for the present invention are safe for long term use, orally absorbed, and have favorable pharmacokinetics. A minimal requirement for the pharmacokinetics is that the level of circulating tracer falls to a baseline between scheduled drug doses and can be accurately detected. Most critically, the tracer is transdermally detectable.

Transdermal Detection Device

The transdermal detection device of the present invention is preferably a small apparatus that can be worn continuously by the patient. Some embodiments that may be suitable comprise a wristwatch, earring or necklace-type configuration. The device is able to detect a signal, such as a fluorescent signal, transdermally. Transdermal sensing is described for example in the following references, each of which is incorporated by reference in its entirety: Lakowicz J. R. Emerging Application of Fluorescence Spectroscopy to Cellular Imaging: Lifetime Imaging, Metal-Ligand Probes, Multi-Photon Excitation and Light Quenching, *Scanning Microscopy Supplement* 10:213–224 (1996); Tolosa L. et al. Optical Assay for Glucose Based on the Luminescence Decay Time of the Long Wavelength Dye Cy5™, *Sensors and Actuators* B 45:93–99 (1997); Guo et al. Use of Long-Lifetime Re(I) Complex in Fluorescence Polarization Immunoassays of High-Molecular-Weight Analytes, *Anal. Chem.* 70:632–637 (1998); Youn et al. Fluorescence Energy Transfer Immunoassay Based on a Long-Lifetime Luminescent Metal-Ligand Complex, *Anal. Biochem.* 232:24–30 (1995); and Lakowicz et al. Emerging Biomedical and Advanced Applications of Time Resolved Fluorescence Spectroscopy, Journ. of Fluorescence 4(1):117–136 (1994).

The teaching of transdermal monitoring in U.S. Pat. No. 5,628,310 by Rao et al. which is incorporated herein in its entirety, may also be utilized in carrying out the methods of the present invention.

A preferred embodiment of the present invention comprises a device held in close contact with the skin of a person. A highly preferred embodiment comprises a transdermal detection device that is able to detect ingestion of a drug wherein the drug is labeled or tagged with a tracer compound such as a fluorescent dye.

Signal Transmission System

The third element of the remotely monitored therapy system comprises a signal transmission system. The signal transmission system relays the detected signal to a receiving base, where the signal can then be interpreted and responded to. In a preferred embodiment, the system operates automatically, requiring no effort on the part of the patient. For example, one preferred embodiment is a portable telephone, using either cellular or digital, technology, or radio-telephone technology. Since each of these technologies are experiencing rapid decreases in costs and increasing miniaturization, use of such instruments is both economically and practically feasible.

To minimize the effort required on the part of the patient, signal transmission functions automatically, and a reading is transmitted hourly, or according to any desired periodic reading. This allows the receiving system to plot the level of the tracer continuously, and to determine, within any desired period of time, when the therapeutic drug dose was ingested.

Signal Receiving System

The fourth principal component of the present invention is a signal receiving system. The signal receiving system receives signals from the transdermal monitoring device via the signal transmission system, and then interprets the signal and triggers and suitable response. Such a system may be centrally located for example, at a public health or medical facility assuming responsibility for the patient, or it might be more centralized as is common for cardiac event monitoring. Either way, the supervising physician or public health official receives a periodic read out of all patients who have taken their medication as instructed, and a list of any patients who have been nonadherent.

In one preferred embodiment of the present invention, the signal transmitting system and the receiving system have two-way communications. This allows enables/enhancers to be incorporated, such as a reminder call to take the medicine, follow-up calls if the reminder went unheeded, and thank you calls when drug ingestion is confirmed. Additional calls to remind patients of scheduled clinic visits can also improve adherence with all aspects of treatment. Importantly, like directly observed therapy, remotely monitored therapy documents noncompliance, a necessity for making a legally defensible decision to transfer nonadherent patient to a more restrictive therapy option.

In another preferred embodiment, a patient ingests a pill (capsule, etc.) that contains a tracer dye (fluorophore) such as indocyanine green (IcG). The dye is transported through the circulatory system to blood vessels just under the skin. The change in modulation of intensity of the emitted light is detected by an external sensor. The external sensor is embedded within a transdermal device which is placed upon the patient's skin above a layer of ruthenium doped plastic film. The increase in modulation of the emitted light is compared to the modulated light (baseline) prior to ingestion. The magnitude of the measured modulation is proportional to the concentration of the dye. The system monitors the presence of the dye thereby indicating positive or negative compliance.

An especially desirable use of the present invention is monitoring compliance with therapeutic regimens for people with tuberculosis. The ability to detect whether a patient has taken his medicine, and thus determine whether the treatment is effective, is highly desirable with the rise in drug-resistant mycobacteria. A preferred method includes attaching a detection device to an individual to monitor drug compliance. During the course of treatment, drug compliance is recorded by a central signal receiving location and reminders are sent to patients when they fail to take their medication. An important result of this system is the ability to detect drug-resistant strains. For example, if a patient is monitored for compliance, and despite confirmed compliance it is discovered that he is still suffering from tuberculosis at the end of the prescribed drug regimen, the supervising healthcare provider may then be alerted to an infection caused by a drug-resistant strain. At this time, the treatment could be changed, the drug sensitivity of the infecting mycobacteria could be determined, or the same treatment could be continued for a longer amount of time.

The ease of administration is a particularly beneficial aspect of the present invention. For example, children are not intimidated by the application of a transdermal device, such as a wristwatch, and are not hesitant to wear such a device for a time sufficient to monitor drug therapy. Such transdermal devices are also easily stored and transported to isolated places that may lack materials or technical resources to conduct more involved tests such as those requiring chemical analysis. The present invention can be made from inexpensive materials that can be produced at low cost and used by health care organizations.

In a preferred embodiment of the present invention, a compliance monitoring system directed to measuring drug compliance by a non-invasive optical measurement is provided. The concept requires labeling a drug with a signalling component such as a red or near infrared fluorophore. As demonstrated in the Example, the emission of such fluorophores, even at micromolar concentrations, can be detected through skin. In our novel approach the sensor which is placed against the skin contains a long lifetime fluorophore in a plastic film. The tissue is illuminated with intensity modulated light with a frequency near 2 MHz. The presence of fluorophore in the tissue can be detected from the modulation of the emission, which represents the intensity of the fluorophore in tissues relative to that of the long lived reference. Such measurements can be accomplished with simple hand held devices in the doctor's office or at the point of care.

As described in more detail in the Examples below, the effectiveness of fluorescent markers was evaluated using indocyanine G (IcG) and rhodamine 800 (Rh800). More specifically, different concentrations of IcG and Rh800 in 0.5% intralipid (a model for chicken or bovine tissue), and in chicken tissue were measured using modulation measurements. These measurements were conducted using a long lifetime ruthenium complex in a film as a reference fluorophore. Modulation values at each dye concentration were equivalent to the fractional intensity of the dye emission present in the system, thereby making modulation values a measure of dye concentration. The results of these measurements demonstrated that these dyes can be detected non-invasively through the human skin using appropriate instrumentation. Concentrations of as low as 50 nM for Rh-800 (Table II, as shown in FIG. 21) and 250 nm for IcG (Table V, as shown in FIG. 24) were detected in this study reflecting the sensitivity of this technique.

In one embodiment of the present invention, the modulation measurements are used to monitor compliance by formulating medications with IcG. IcG is currently used for different purposes in humans, and it is known that IcG is rapidly cleared from circulation. Since administered drugs will not necessarily be cleared from the circulation at the same rate as IcG, the methods of the present invention comprise compositions wherein IcG is formulated in a time release fashion to market the known clearance rates of administered drugs. Evidence for the injection of drugs can then be determined non-invasively by the measurement of the modulation of the emission seen through the skin.

Figure 17:
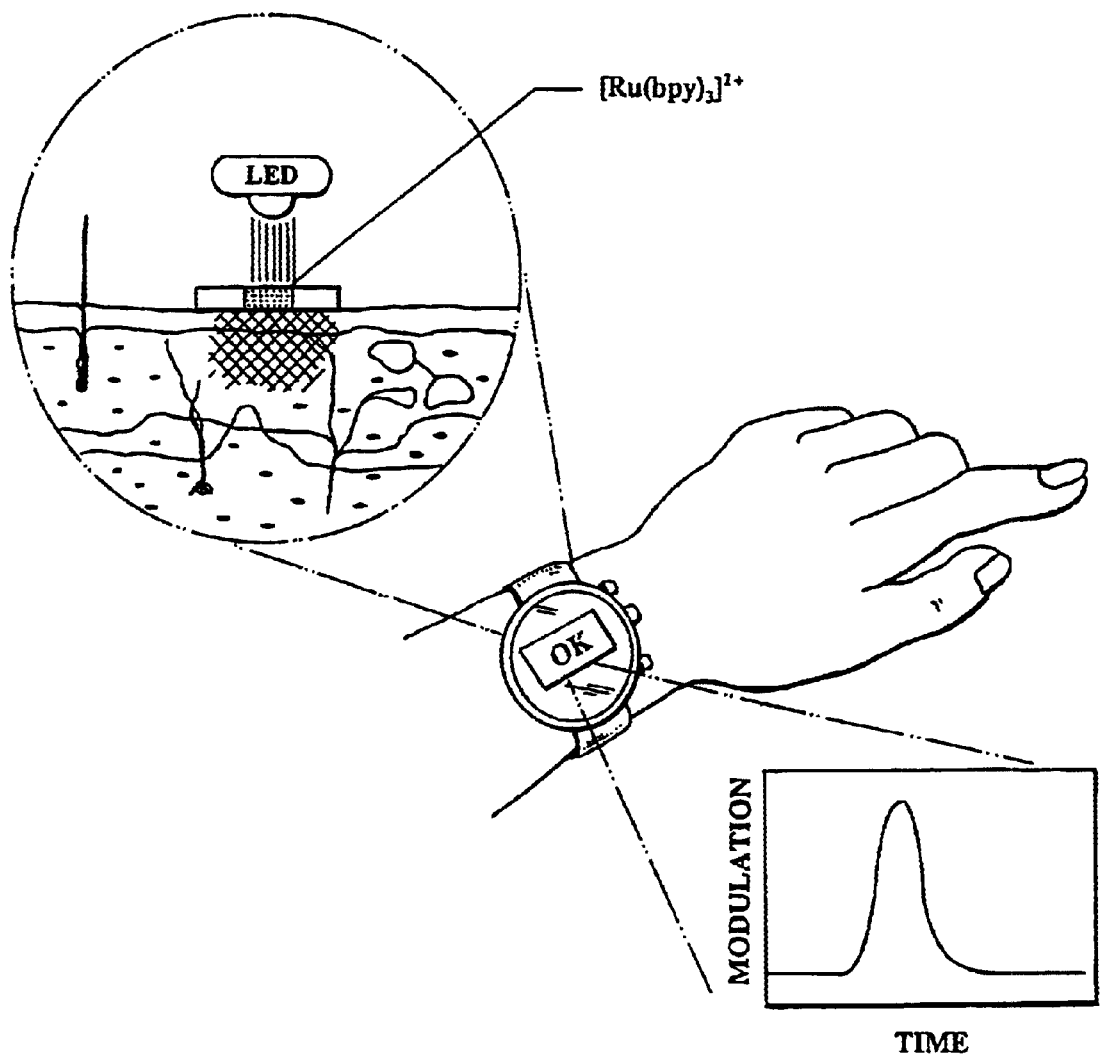
FIG. 17 is a schematic showing a proposed device for non-invasive compliance monitoring.

With currently available opto-electronics technology, a hand held battery powered hand device, such as a wristwatch, for the measurement of modulation can be readily built (FIG. 17). The light source may comprise a light emitting diode (LED) or a laser diode. The output of these light sources can be easily modulated to 50 MHz or higher (35–37) and with present technology, a portable monitor can be routinely used each time a chronically ill patient is seen by a health care professional.

The compliance monitoring system of the present invention is useful for monitoring therapeutic compliance in a variety of diseases and disorders, including, but not limited to infectious diseases (staphyloccal, streptococcal, pneumococcal, niesseria, listeriosis, enterobacteriaceae, salmonella, pseudomonas, cholera, treponematoses, histoplasmosis, coccidioidomycosis, mycobacterial, cryptococcosis, aspergillosis, rickettsial, chlamydial, viral, parasitic and sexually transmitted diseases), immunodeficiency diseases (acquired immunodeficiency syndrome), cardiovascular disorders (endocarditis, pericardial disease, erythromelalgia), pulmonary disorders (bronchitis, pneumonia), gastrointestinal, (functional dyspepsia, peritonitis), hepatic and biliary disorders, endocrine disorders (diabetes mellitus, hypoglycemia, hyperthyroidism, hypothyroidism), cancer, musculoskeletal and connective tissue disorders (rheumatoid arthritis, gout, osteoporosis), neurologic and psychiatric disorders (insomnia, multiple sclerosis, epilepsy), genitourinary disorders (renal disease, kidney infection, nephritic syndrome, bacterial pyelonephritis) and other physiological disorders and diseases.

In addition, numerous therapeutic agents may be used in the present invention, including, but not limited to, antimicrobial agents, antibiotics, antivirals, antidepressants, β-lactam antibiotics, aminoglycosides, macrolides, lincomycin, clindamycin, tetracyclines, quinolones, polypeptides, sulfonamides, trimethoprims, sulfamethoxazoles, growth factors, lipids, and neurotransmitters. Furthermore, vitamins, and minerals may also labeled for use in the present invention, especially for patients suffering from nutritional or metabolic disorders. The monitoring system of the present invention is also useful when conducting clinical trials for assuring therapeutic compliance by participants.

An important advantage of the present invention is that it can function effectively and accommodate discrepancies such as those resulting from variations in dermal pigmentation, thickness, and vascularity.

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE

The following experiment was conducted in order to measure the presence and concentration of fluorophores in scattering media, including intralipid suspensions, chicken skin and chicken muscle. The fluorophores were rhodamine 800 (Rh800) and indocyanine green (IcG), both of which would be excited at long wavelengths not absorbed by tissues. It is known to be difficult to quantify the fluorescence intensity from probes in scattering media. This problem was solved using modulated excitation near 2 MHz and a long lifetime reference fluorophores in a polymer film placed immediately on the illuminated surface of the sample. Under these conditions, the modulation of the emission is a measure of the intensity of the fluorophore (Rh800 or IcG) relative to the long lifetime reference. Using this method we were able to measure the concentration dependent intensities of Rh800 and IcG in an intralipid suspension. Additionally, micromolar concentrations of these probes could be detected in chicken muscles, even when the muscle was covered with a layer of chicken skin. Based on the findings of this study, we have demonstrated successful use of transdermal detection of long-wavelength fluorophores as a non-invasive method to monitor patient compliance in taking medicines used for treatment of chronic diseases such as tuberculosis and AIDS.

Materials and Methods

Rhodamine 800 (Rh800) was obtained from Lambda Physik, and indocyanine green (IcG) from Sigma (St. Louis, IVIO), and were used without further purification. For aqueous solution, the probes were dissolved in water. Intralipid (20%) was obtained from KabiVitrum, Inc (Clayton, N.C.). The intralipid was diluted 40-fold into buffer, to 0.5%, to provide a sample with scattering properties comparable to that of tissues like chicken or bovine muscles. Based on available data [7] the effective scattering coefficient (1-g) (for 0.5% intralipid can be estimated as 7.25 cm$^{-1}$. Concentrations of Rh800 and IcG were determined from the extinction coefficients of $8.95 \times 10^4$ L mol$^{-1}$ cm$^{-1}$ at 682 nm and at 780 nm, respectively.

Figure 18:
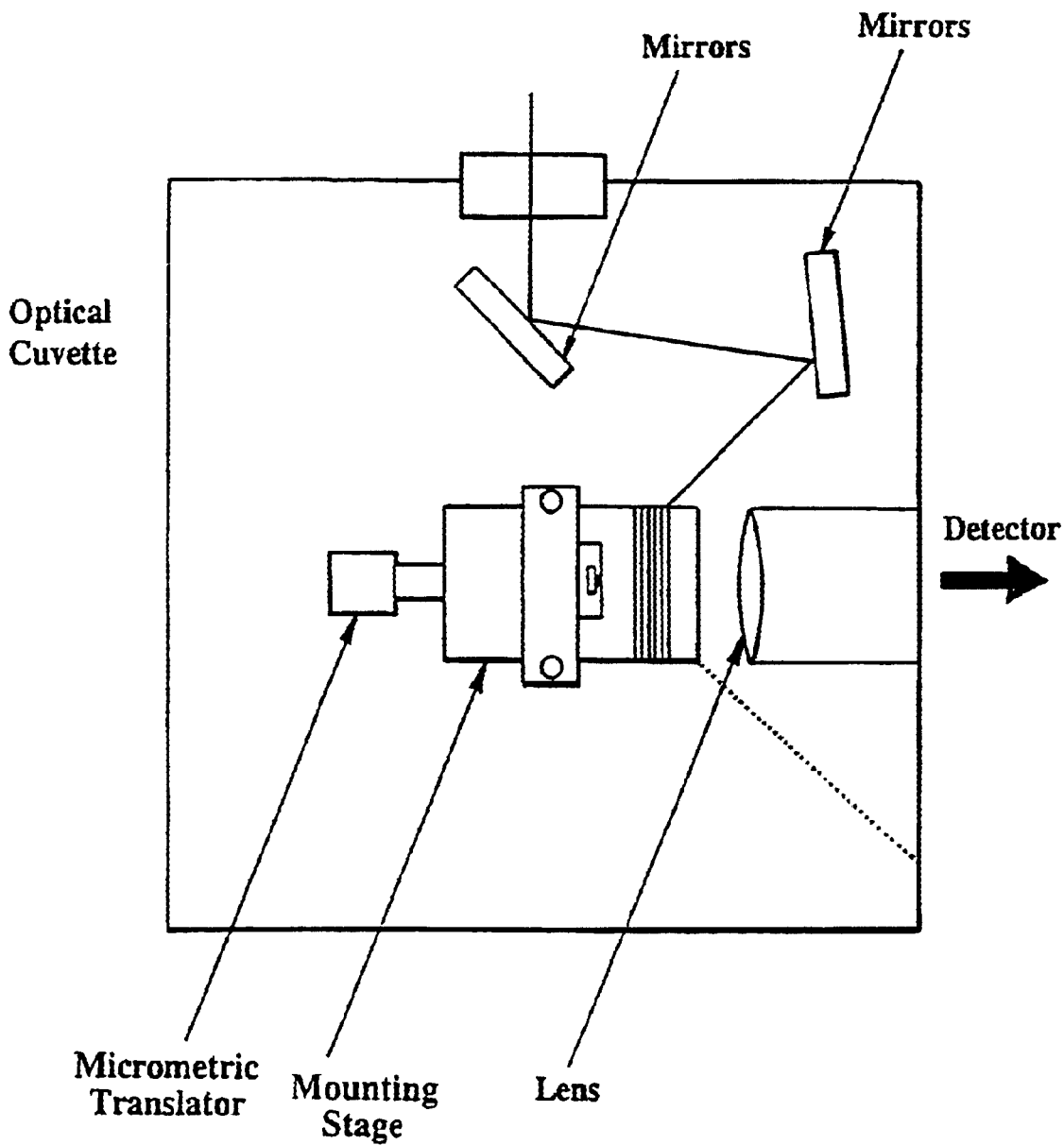
FIG. 18 is a schematic showing a sample holder used for conducting fluorescence measurements using front-face illumination and detection.

All fluorescence measurements were performed using front-face illumination and detection, using the sample holder shown in FIG. 18. The incident light was redirected from the usual position using two mirrors. The position of the sample could be adjusted with a movable stage. The re-emergent light passed through one or more optical filters prior to reaching the destination.

Figure 19:
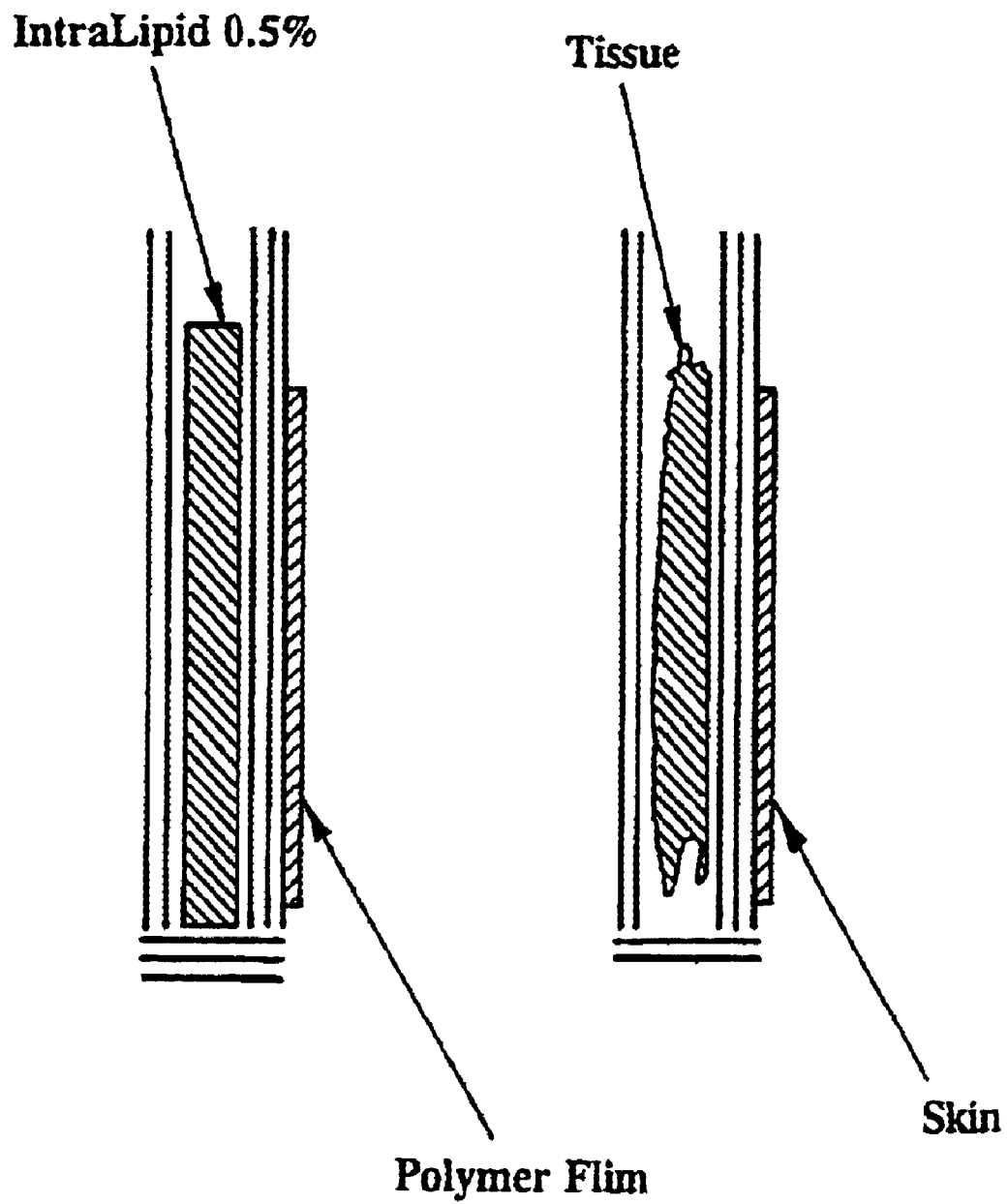
FIG. 19 is a schematic showing sample configuration for fluorescence measurements in intralipid or in chicken tissue. The sample consisted of either a cuvette containing the intralipid, or a quartz slide covering the chicken muscle and skin.

The sample consisted of either a cuvette containing the intralipid, or a quartz slide covering the chicken muscle and skin (FIG. 19). Excitation at 600 nm was provided by the fundamental output of a rhodamine 6G dye laser. This dye laser was synchronously pumped by a mode-locked argon ion laser, and cavity dumped at 1.88 MHz.

Frequency domain intensity decay measurements were performed as described previously [8–11]. Phase angles and modulation measurements at frequencies greater than 1.88 MHz were accomplished using the harmonic content of the picosecond pulses [12–14]. The excitation was polarized vertically, and the emission detected without an emission polarizer. The re-emergent light was either observed directly, or through two cut-off filters (630 and 660 nm) to remove scattered light and/or attenuate the fluorophore emission relative to that of the long lived reference.

A long lifetime reference signal was provided by [Ru(bPY)$_2$(dppz)](PF$_6$)$^2$ in a polyvinyl alcohol (PVA) film, where bpy is 2,2'-bipyridine and dppz is dipyrido[3,2-a:2',3'-cl]phenazine. Such metal-ligand complexes are known to display lifetimes from 100 ns to 13 (s [15–16]. The intensity decay time of [Ru(bpy)$_2$(dppz)](PF$_6$)$_2$ in the PVA film was near 800 ns (Table 1 as shown in FIG. 20).

Analysis

The intensity decay data was analyzed in terms of the multi-exponential model $$I(t) = \sum_i \alpha_i \exp(-t/\tau_i) \qquad (1)$$

In this expression $\alpha_i$ represents the pre-exponential factors associated with each lifetime $\tau_i$. The fractional contribution of each decay time component to the steady state intensity is given by $$f_i = \frac{\alpha_i \tau_i}{\sum_j \alpha_j \tau_j}. \qquad (2)$$

The values of $\Sigma \alpha_i$ and $\Sigma f_i$ are typically normalized to unity. The mean lifetime is given by $$\bar{\tau} = \sum_i f_i \tau_i = \sum_i \frac{\alpha_i \tau_i^2}{\alpha_i \tau_i}. \qquad (3)$$

In the frequency-domain measurements the measured quantities are the phase shift of the emission ($\phi_{107}$) and its modulation (m$_{107}$) at the light modulation frequency $\omega_i$ in radians/sec. The values of $\alpha_i$ and $\tau_i$ are determined by non-linear least squares fitting and minimization of the goodness-of-fit parameter $X^2_R$.

$$\chi_R^2 = \frac{1}{\nu} \sum_{\omega,k} \left(\frac{\phi_\omega - \phi_{c\omega}}{\delta\phi}\right)^2 + \frac{1}{\nu} \sum_{\omega,k} \left(\frac{m_\omega - m_{c,\omega}}{\delta m}\right)^2 \qquad (4)$$

In this expression the subscript c refers to calculated values of $\phi_\omega$ and m$_\omega$ for assumed values of $\alpha_i$ and $\tau_i$ and $\nu$ is the number of degrees of freedom. $\delta\omega$ and $\delta m$ represent the uncertainties in the measured values. In some cases we performed a global analysis of data measured at more than one fluorophore concentrations. In this case the sum in equation 3 extends over these multiple concentrations (k).

The values of $\phi_{\omega c}$ and m$_{\omega c}$ can be calculated for many assumed values of $\alpha_i$ and $\tau_i$. These values are given by $$\phi_{\omega c} = N_\omega / D_\omega \qquad (5)$$

$$m_{\omega c} = (N_\omega^2 + D_\omega^2)^{1/2} \qquad (6)$$

where $$N_\omega = \int_0^\infty I(t) \sin \omega t \, dt = \sum_i \frac{\alpha_i \omega \tau_i^2}{1 + \omega^2 \tau_i^2} \qquad (7)$$

$$D = \int_0^\infty T(t) \cos \omega t \, dt = \sum_i \frac{\alpha_i \tau_i}{1 + \omega^2 \tau_i^2}. \qquad (8)$$

The principle of low frequency modulation sensing can be understood by a rearrangement of equations (5–8). Suppose the sample displays two decay times. Assume further that one decay time is long (L) comparable to the modulation frequency and the other is a typical ns decay time (S). For these conditions the sine and cosine transforms are given by $$N_\omega = f_s m_s \sin \omega \tau_s + f_L m_L \cos \omega \tau_L \qquad (9)$$

$$D_\omega = f_s m_s \cos \omega \tau_s + f_L m_L \sin \omega \tau_L \qquad (10)$$

If the $\omega\tau_L$ product is much greater than unity, then the modulation ($m_L$) of this component is near zero. Under the condition the observed modulation is given by $$m_{obs}=[(f_s m_s \sin \omega\tau_s)^2 (f_L m_L \cos \omega\tau_L)^2]^{1/2} \tag{11}$$

The modulation frequency can be selected so that $m_s$ is near 1.0. Then, the observed modulation is $$m_{obs}=f_s \tag{12}$$

and represents the fractional intensity of the fluorophore with the short lifetime.

Results

Spectra Properties of Rh800 and IcG

For the present studies we used two fluorophores with ns decay times, Rh800 and IcG, and a long lifetime metal ligand complex. We refer to this long lifetime reference as the Ru complex (FIG. 1). Absorption and emission spectra of these probes are shown in FIG. 2. All three fluorophores can be excited at 600 nm. In water Rh800 emits maximally near 706 nm, and IcG near 805 nm. The Ru complex is essentially non-fluorescent in water [17–18] but becomes fluorescent in non-polar environments which prevent contact with water. The emission spectra of Rh800 and IcG in 0.5% intralipid is similar to those observed in water (FIG. 2).

Indocyanine green (IcG) is approved for use in humans, and is widely used in opthamology for studies of liver and kidney functions, to measure blood volume, and to estimate the severity of burns [19–25]. While the near infrared (NIR) absorption and emission of IcG in tissues can be readily detected, it is known that the spectral properties of IcG are complex [29–31]. IcG appears to aggregate in aqueous solution with the aggregates being less fluorescent than the monomeric species. In biological samples IcG associates with proteins and lipids, with the intensity being dependent on the total concentration of IcG as well as on the concentration of macromolecules which bind IcG. Hence we examined the dependence of the intensity on the concentration of IcG and Rh800.

Figure 3:
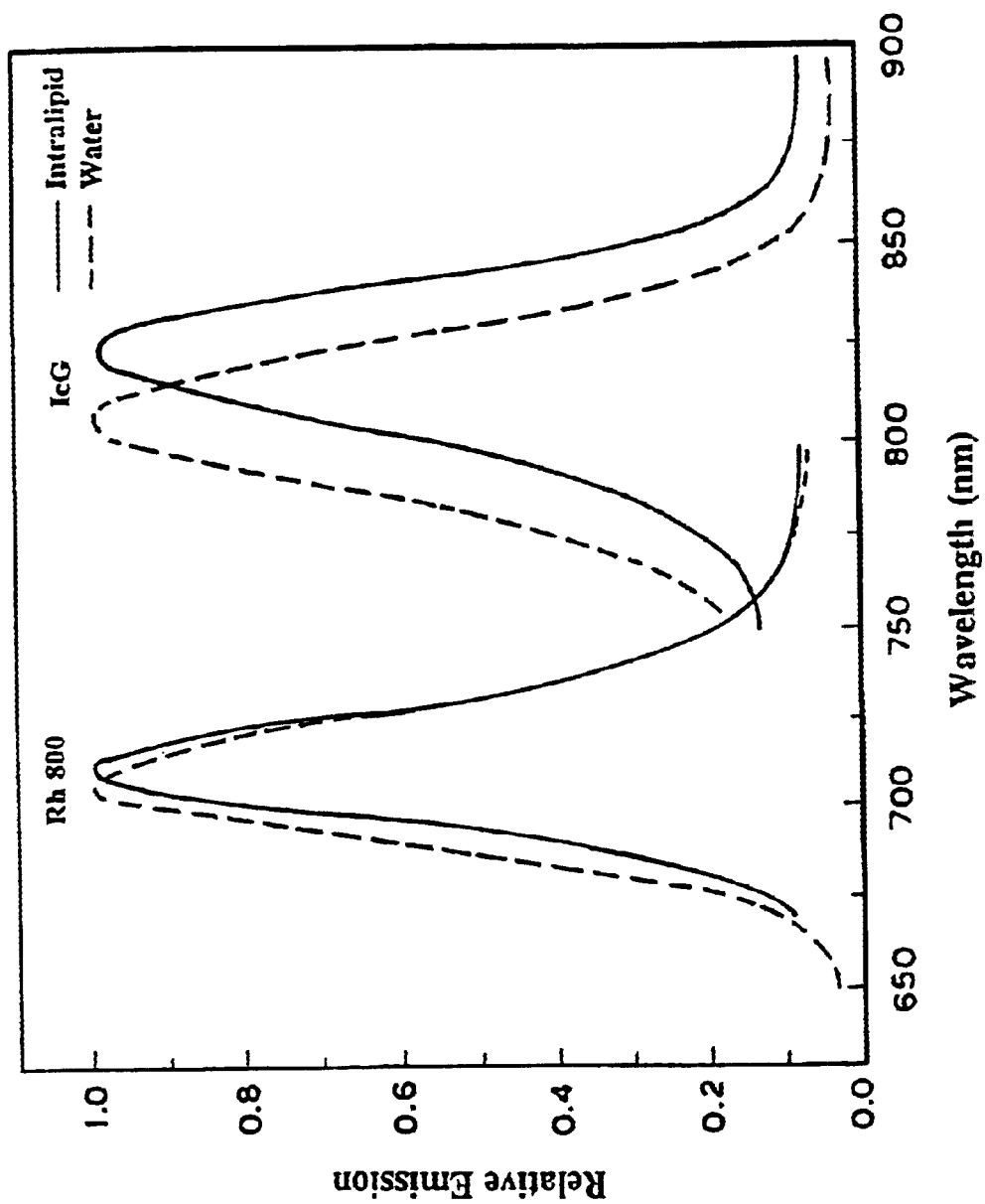
FIG. 3 provides emission spectra of Rh800 ($\mu$M) and IcG ($\mu$M) in 0.5% intralipid solution. Also shown in dashed lines are the emission spectra in water.
Figure 4:
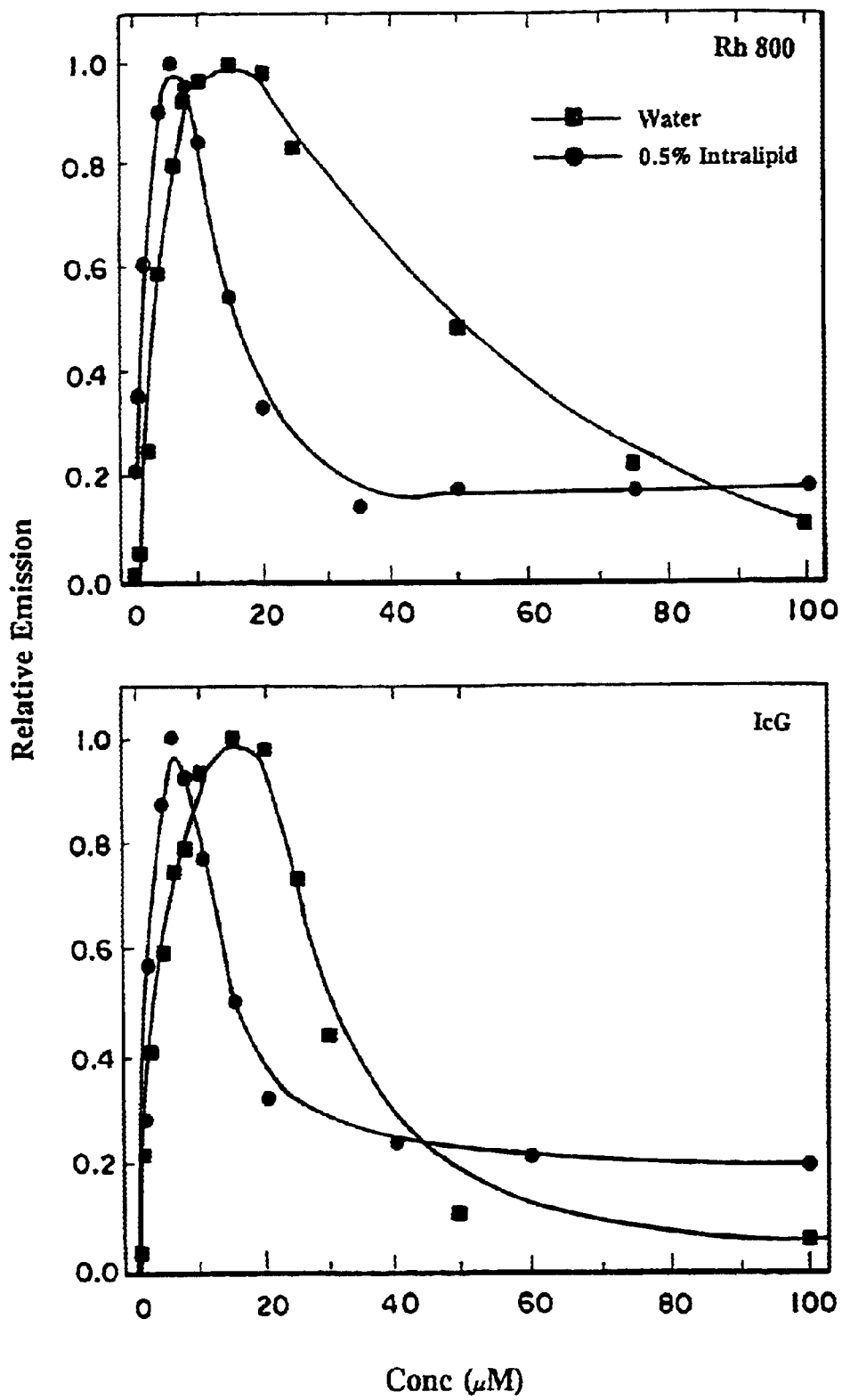
FIG. 4 provides graphs showing concentration dependence of fluorescence intensity of Rh800 and IcG in water and 0.5% intralipid solution.

The concentration-dependent intensities of Rh800 and IcG are shown in FIG. 4. For both fluorophores the emission intensity initially increased, and then decreased as the probe concentration increased above 10 to 20 $\mu$M. The peak intensity was found to occur at lower concentrations in 0.5% intralipid than in water. Though not wishing to be bound by the following theory, we believe the self-quenching of Rh800 and IcG is due to self-association and on energy transfer between the aggregated fluorophores in 0.5% intralipid. The occurrence of the peak intensity at lower probe concentration in 0.5% intralipid suggests that binding to intralipid results in high local concentrations of the fluorophore due to binding to the intralipid micelles.

Figure 5:
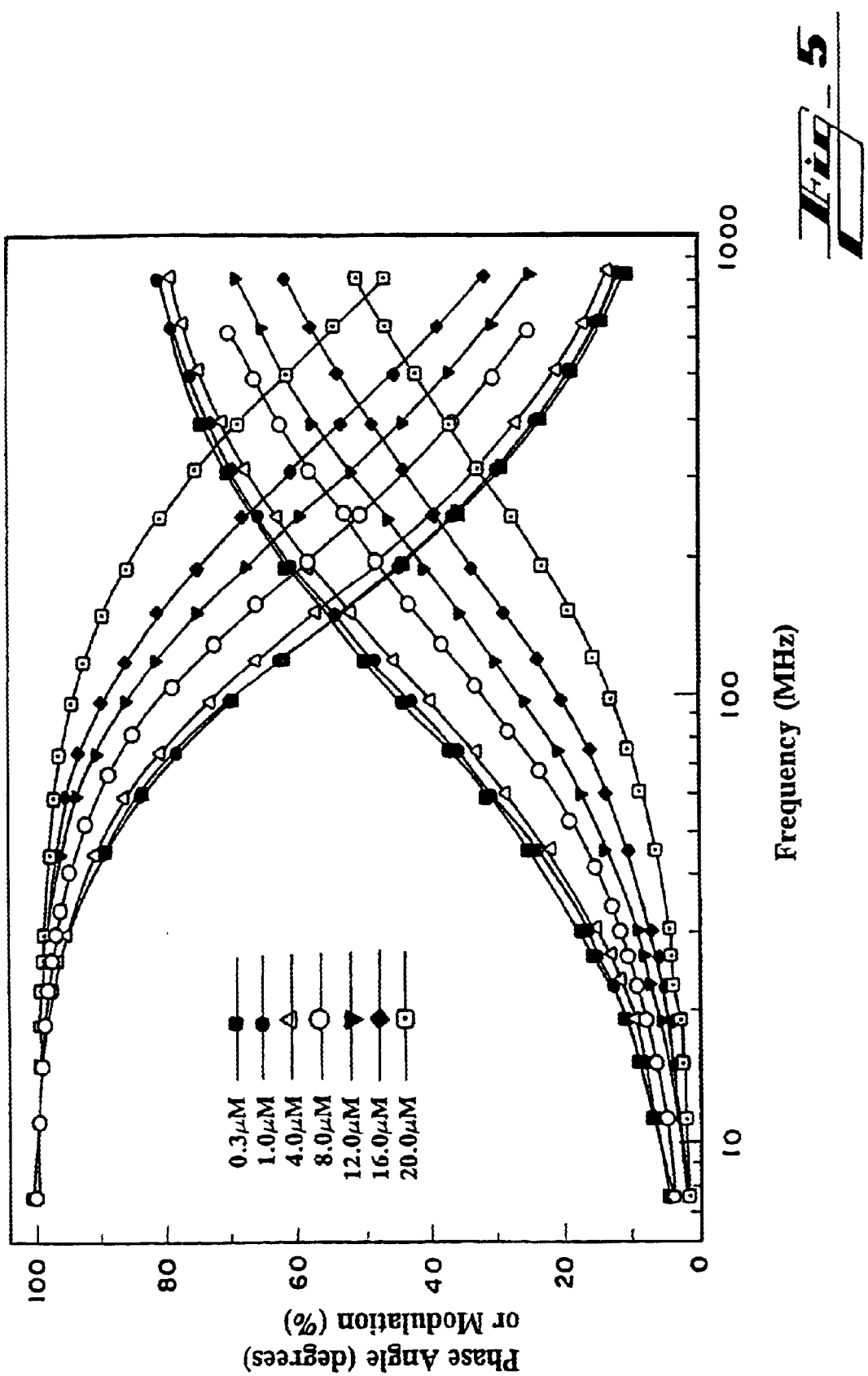
FIG. 5 provides a graph showing phase and modulation frequency responses for different concentrations of Rhodamine 800 in 0.5% intralipid solution.

We examined the frequency-domain intensity decay of Rh800 and IcG in 0.5% intralipid. As the concentration of Rh800 increased the frequency response shifted to higher frequency (FIG. 5). These data were analyzed in terms of the multiexponential model (Table II, as shown in FIG. 21). In water, in the absence of intralipid, Rh800 displayed a single exponential decay of 0.686 ns. In 0.5% intralipid the intensity decay of Rh800 becomes more complex. The data could be fit to a two decay time model. The individual decay times and the mean decay times decreased with increasing Rh800 concentrations (FIG. 6). Similar results are found for IcG, with the decay times and mean decay time decreasing with increasing IcG concentration (Table III, as shown in FIG. 22).

Modulation Sensing of Rh800 in Intralipid

Figure 7:
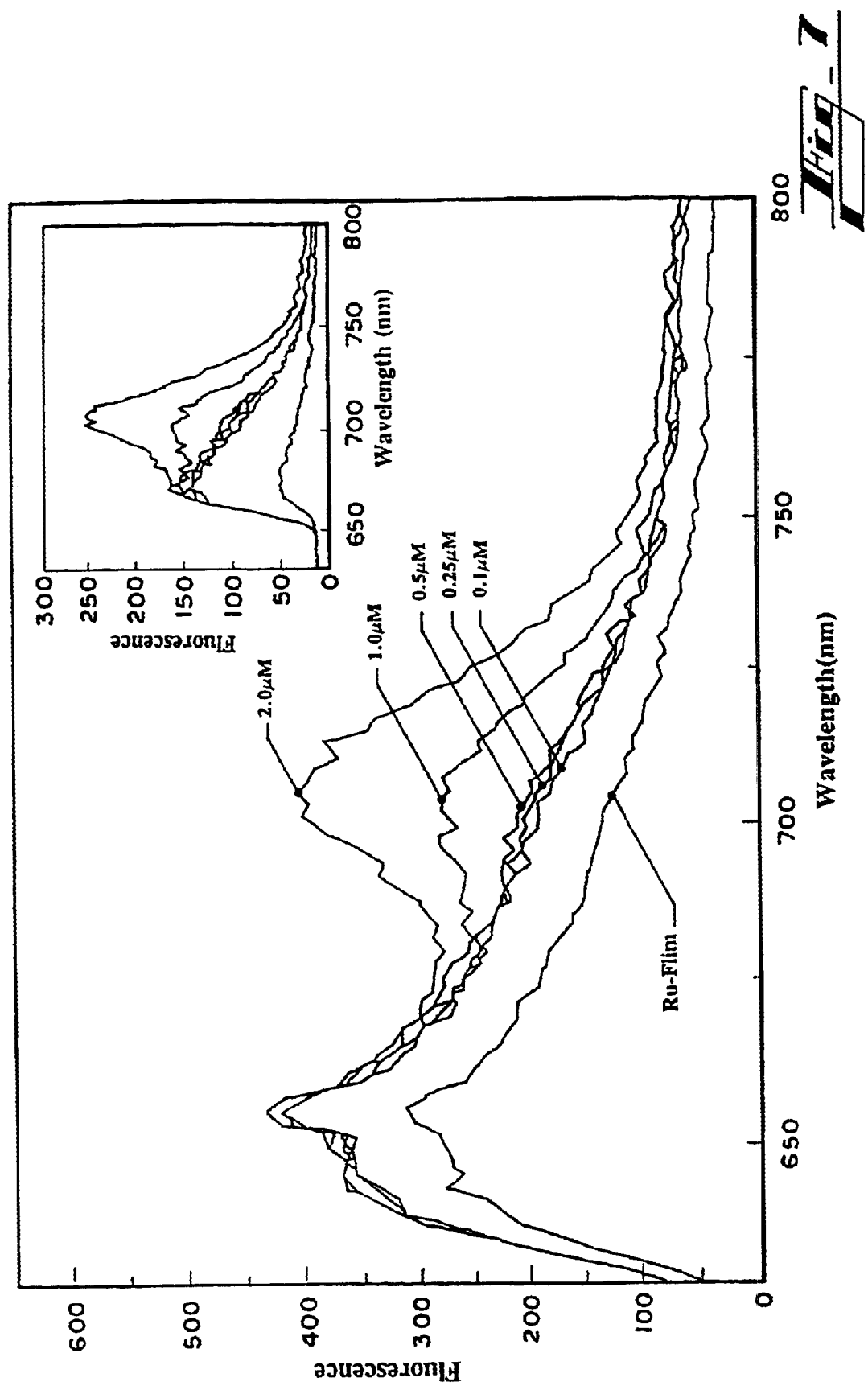
FIG. 7 provides a graph showing the emission spectra of Rh800 in 0.5% intralipid solution in the presence of PVA film containing ruthenium metal ligand complex. The inset shows the emission spectra in the presence of a 630/660 cut off filter. Excitation was at 600 nm.

Concentrations of Rh800 in intralipids were determined by the modulation method. Rh800 was dissolved in 0.5% intralipid. A polyvinyl alcohol film containing the Ru complex was placed on the illuminated surface of the cuvette. Emission spectra are shown in FIG. 7. The peak near 710 nm is due by Rh800. The signal near 650 nm is due to emission from the Ru complex, and also to light scatter from the intralipid. The scattering component was minimized by observing the solution through a combination of two 630 and 660 nm cut-off filters. Under these conditions the signal observed through the filters is mostly due to the Ru complex and Rh800.

Figure 8:
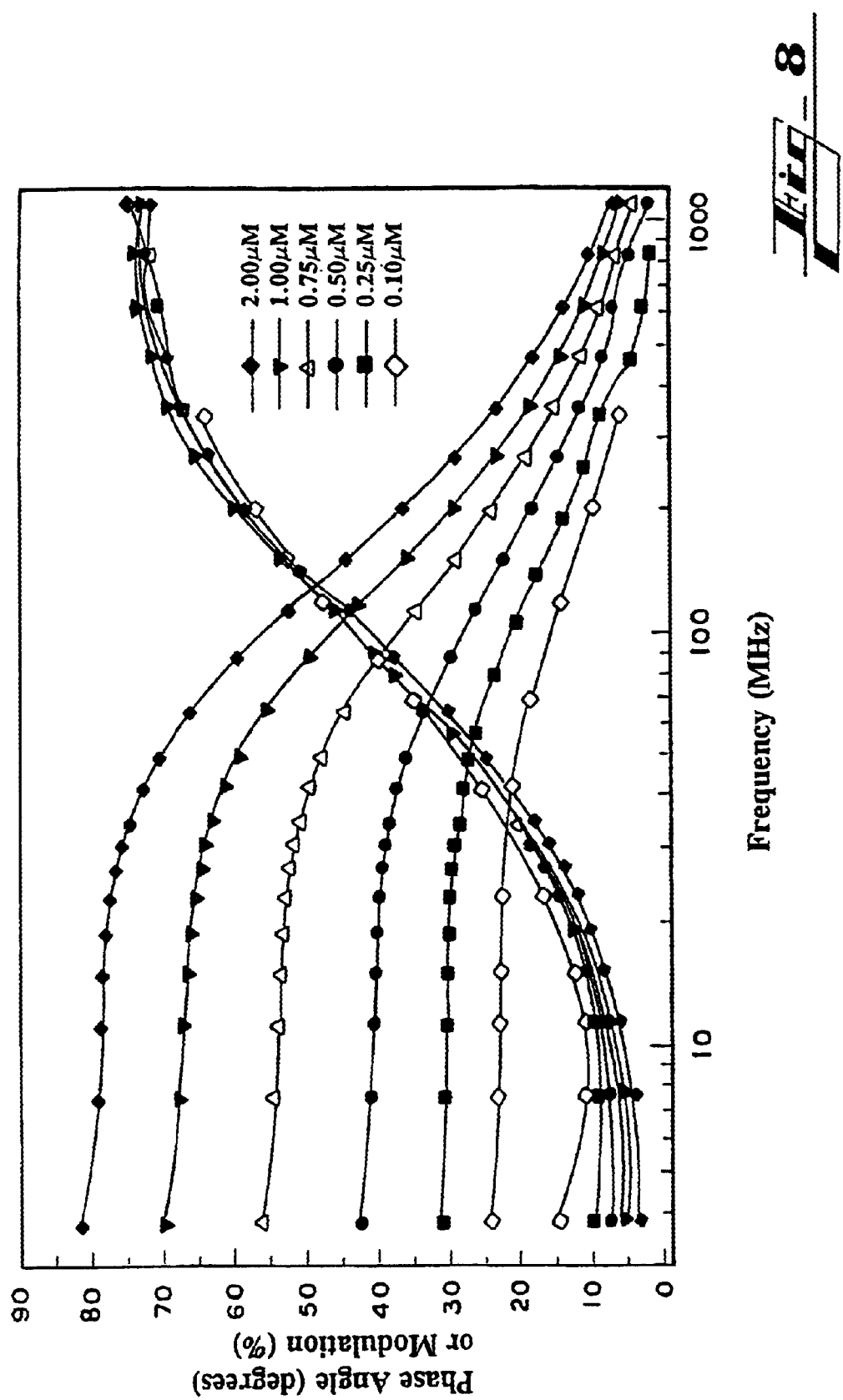
FIG. 8 provides a graph showing phase and modulation frequency responses for different concentrations of rhodamine 800 in 0.5% intralipid solution in the presence of PVA film containing ruthenium complex. Excitation was at 600 nm, and the emission above 660 nm was observed.

Frequency-responses of this combined emission from the Ru complex and Rh800 are shown in FIG. 8. The most dramatic feature of these data are the modulation values from 2 to 20 MHz. The modulation is essentially independent of frequency, and increases as the Rh800 concentration increases. This result is due to the dramatic difference between the decay times of Rh800 in intralipid (1.62 ns) and of the Ru complex (834 ns). The data were globally analyzed in terms of a short and long decay time (Table IV, as shown in FIG. 23). Three decay times of 1.21, 1.62 and 545 ns were found adequate to fit the data of all Rh800 concentrations. As the concentration of Rh800 increased so did the fractional intensity of the short component (Table IV). This result can be understood as due to the combined measurements with the long lifetime standard. At frequencies near 5 MHz the observed modulation is similar to the fractional intensity of the short lifetime Rh800. Modulation values are 0.185, 0.525 and 0.812 (FIG. 8). While calculated $f_s$ values are 0.184, 0.534 and 0.803 (Table IV) at Rh800 concentrations of 0.05, 0.25 and 1.00 $\mu$M, respectively. Hence, the modulation values reflect the contribution of Rh800 to the total emission.

The dependence of the modulation on the Rh800 concentration is shown in FIG. 9. For this concentration range the Rh800 intensity is essentially linear with its concentration (FIG. 4). However, the observed dependence is hyperbolic (FIG. 9). This is the result of normalizing $f_s+f_L$ to unity, so that increasing intensities of Rh800 shift $f_s$ monotonically towards 1.0. The data can be normalized in a different manner to yield a more linear dependence. This is accomplished by normalizing all the values of $f_s$ to the same initial value of $f_L$. Let $f_{L1}$ represent the initial fractional intensity of the long lifetime component, and $f_{Ln}$ the fractional intensity at some higher concentration of the short lived fluorophore. For the initial conditions $$f_{S1}+f_{L1}=1.0 \tag{13}$$

At the next higher concentration of the short lived species one has $$f_{Sn}F_{Ln}=1.0 \tag{14}$$

Let $R=f_{L1}/f_{Ln}$ be the ratio of the long lifetime normalized fractional amplitudes. Then $$Rf_{Sn}+f_{L1}=R \tag{15}$$

Hence the unnormalized modulated amplitude of the short lived component ($f_{Sn}'$) is $$f_{Sn}' = Rf_{Sn} = f_{Sn}\frac{f_{L1}}{f_{Ln}} \tag{16}$$

Using these recalculated fractional amplitude one expected $f_{Sn}'$ or $m_{Sn}'$ approximately linear with the concentration of the short lifetime fluorophore.

These values are shown in the lower panel of FIG. 9, and show that $f_s$ increases in a nearly linear fashion with the Rh800 concentration.

Figure 10:
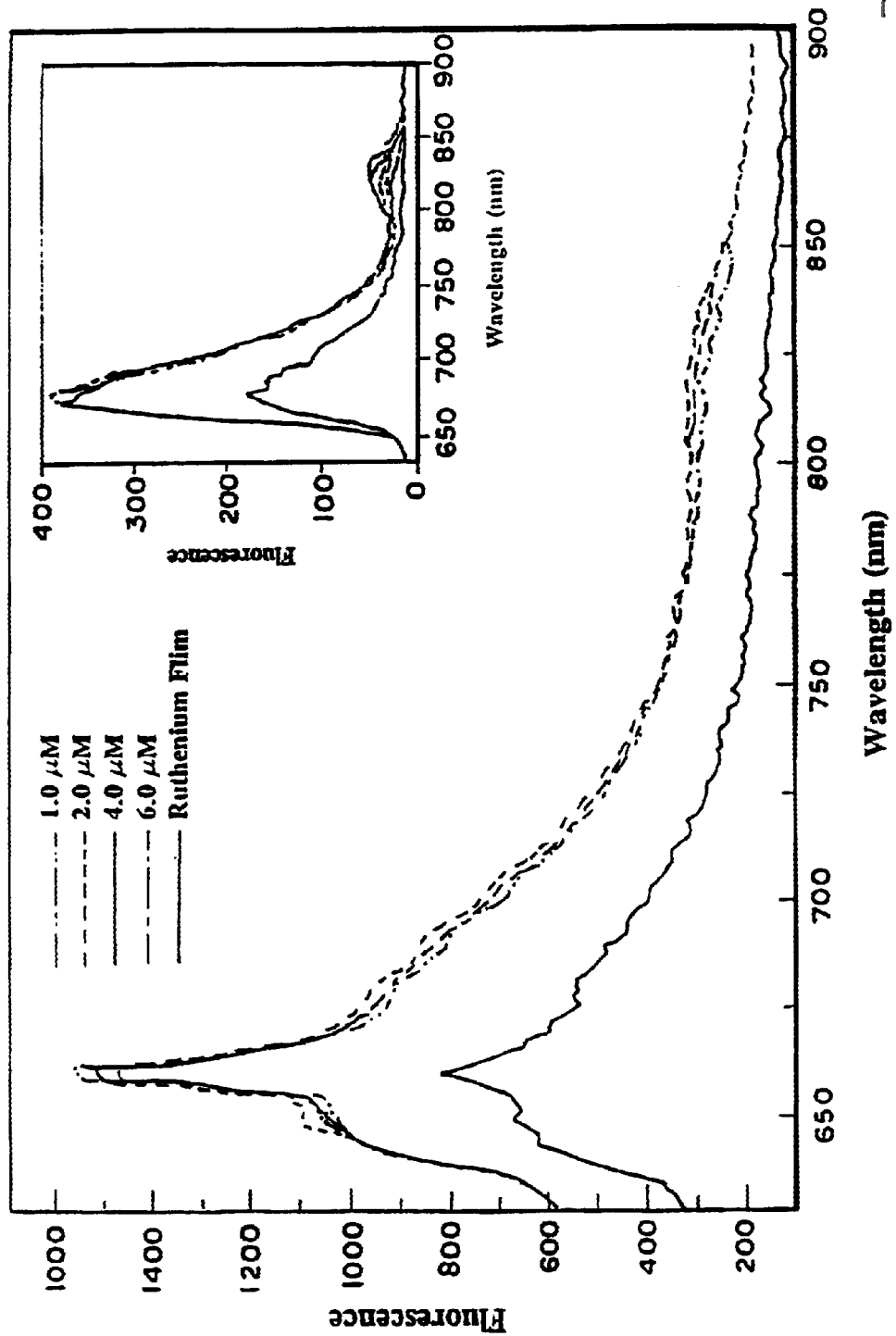
FIG. 10 provides a graph showing the emission spectra of indocyanine green in 0.5% intralipid solution in the presence of the PVA film containing ruthenium metal ligand complex. The inset shows observation in the presence of a 630/660 cut off filter. Excitation was at 600 nm.

Similar experiments were performed with IcG in 0.5% intralipid. The emission of IcG in intralipid occurs near 820 nm, and is considerably weaker than that of Rh800. Emission for the Ru complex is seen near 650 nm, along with some components due to scattered light. The scattered light was removed by the combination of two cut-off filters, resulting in the spectra shown as an insert in FIG. 10.

Figure 11:
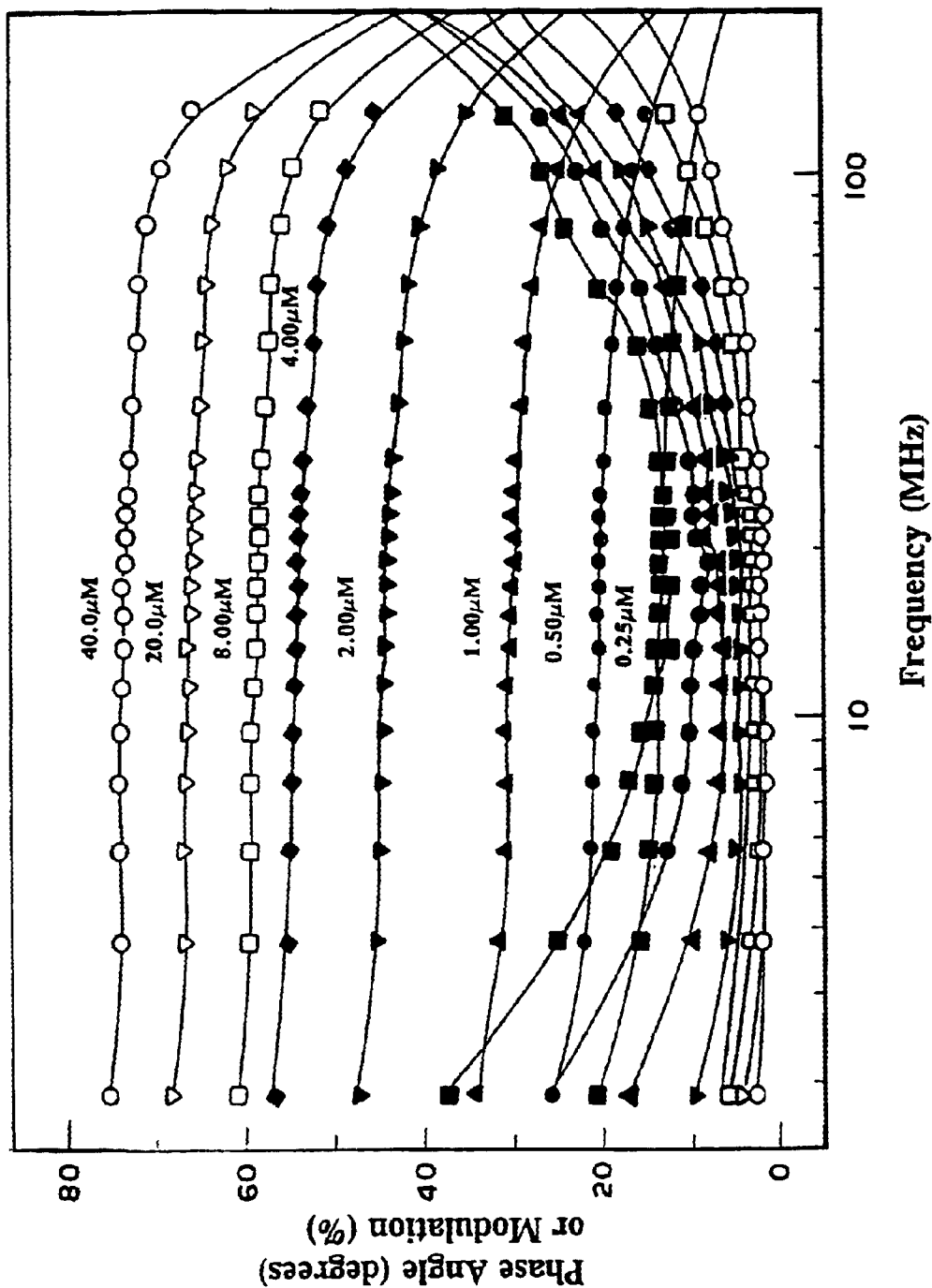
FIG. 11 provides a graph showing phase and modulation frequency response of different concentrations of indocyanine green in 0.5% intralipid solution in the presence of the PVA film containing ruthenium ligand complex. Excitation at 600 nm, and emission observed above 660 nm.
Figure 12:
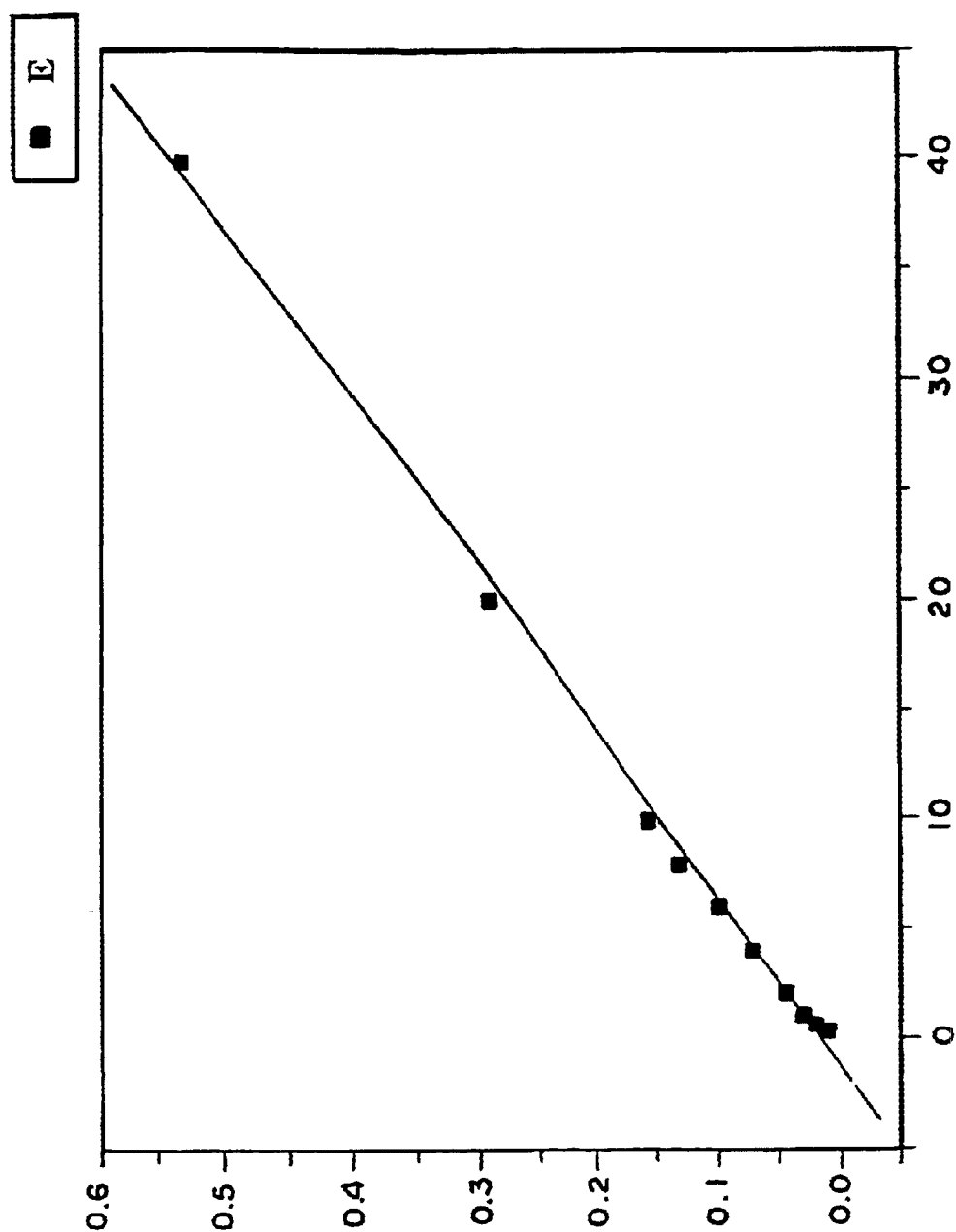
FIG. 12 provides a graph showing 2 MHz modulation of IcG in 0.5% intralipid with the Ru complex reference. The lower panel shows the intensity-normalized modulation ($f_s'$).

Frequency responses for IcG in intralipid are shown in FIG. 11. This sample also had the long lifetime reference. As seen for Rh800, the modulation increased with increasing concentrations of IcG. The modulation at 2 MHz increases hyperbolically with IcG concentration (FIG. 12). The intensity normalized modulation (equation 13) also increased almost linearly. This is somewhat surprising given the previous observations of decreasing intensity with IcG concentration above 20 $\mu$M. At present we believe this difference is due to sample-to-sample variations in the IcG-intralipid samples. The important point is that the concentration of IcG can be estimated from the relatively simple 2 MHz modulation measurement.

Adjustment of Sensor Sensitivity

Figure 13:
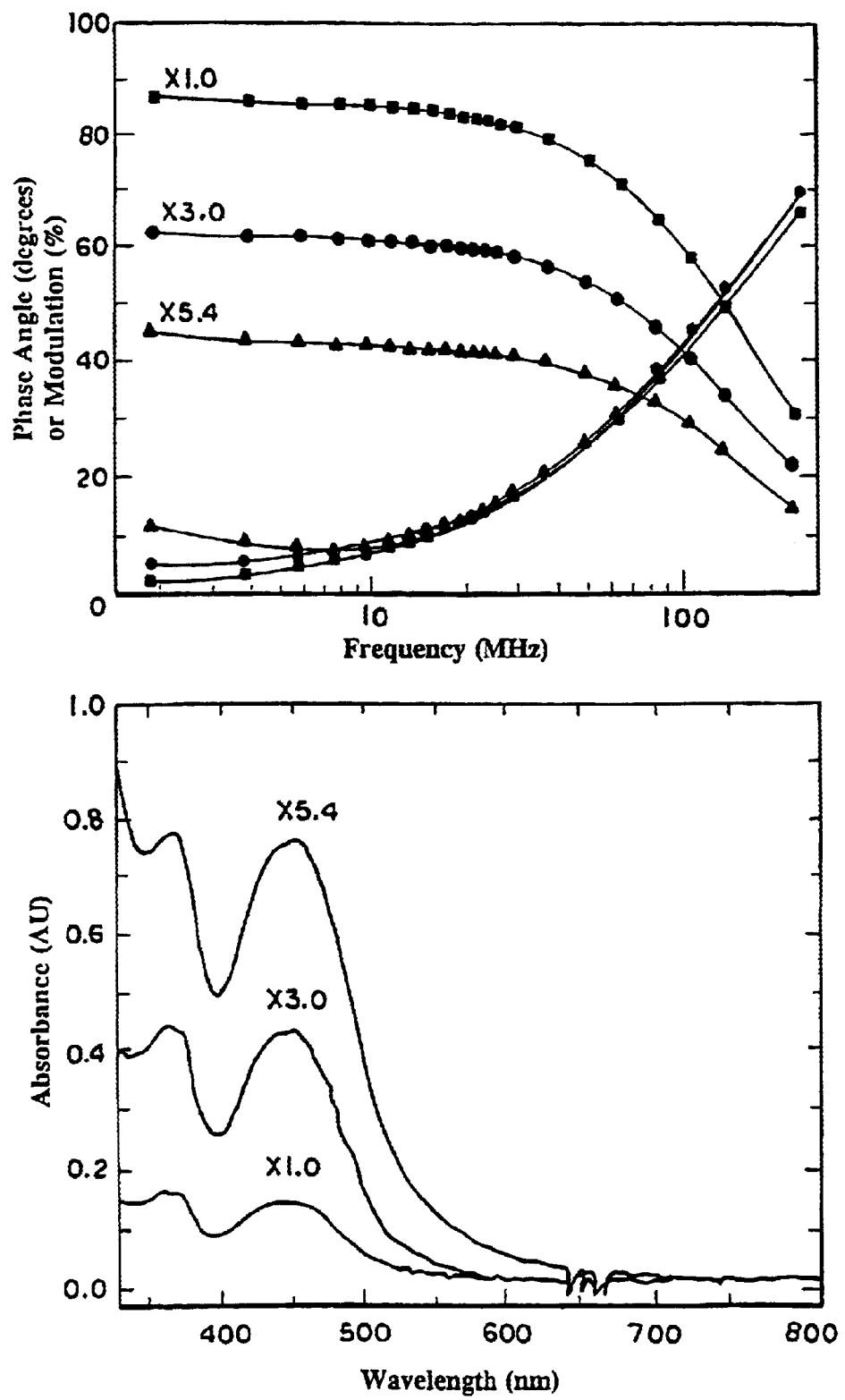
FIG. 13 (Top) provides a graph showing the effect of different ruthenium metal ligand complex concentrations in the PVA film on phase and modulation response of 0.1 $\mu$M rhodamine 800 in 0.5% intralipid solution. (Bottom) provides a graph showing absorbance spectra of the films at the different ruthenium complex concentrations.

A particularly advantageous aspect of the present invention is that it is useful for compliance monitoring over a range of fluorophore concentrations, and also for a range of skin types. One feature that makes this possible is that the sensitivity of the invention can be easily adjusted. This is shown in FIG. 13, where the Rh800 concentration was held constant, and the concentration of the Ru complex was altered. As the concentration and intensity of the reference was increased, the modulation decreased. This occurs because the fractional intensity of the long lifetime component increases. In a real world application the sensor head could contain several reference films allowing the sensitivity to be adjusted as appropriate for a given circumstance.

Detection of Fluorophore Through Skin and or Tissues

Figure 14:
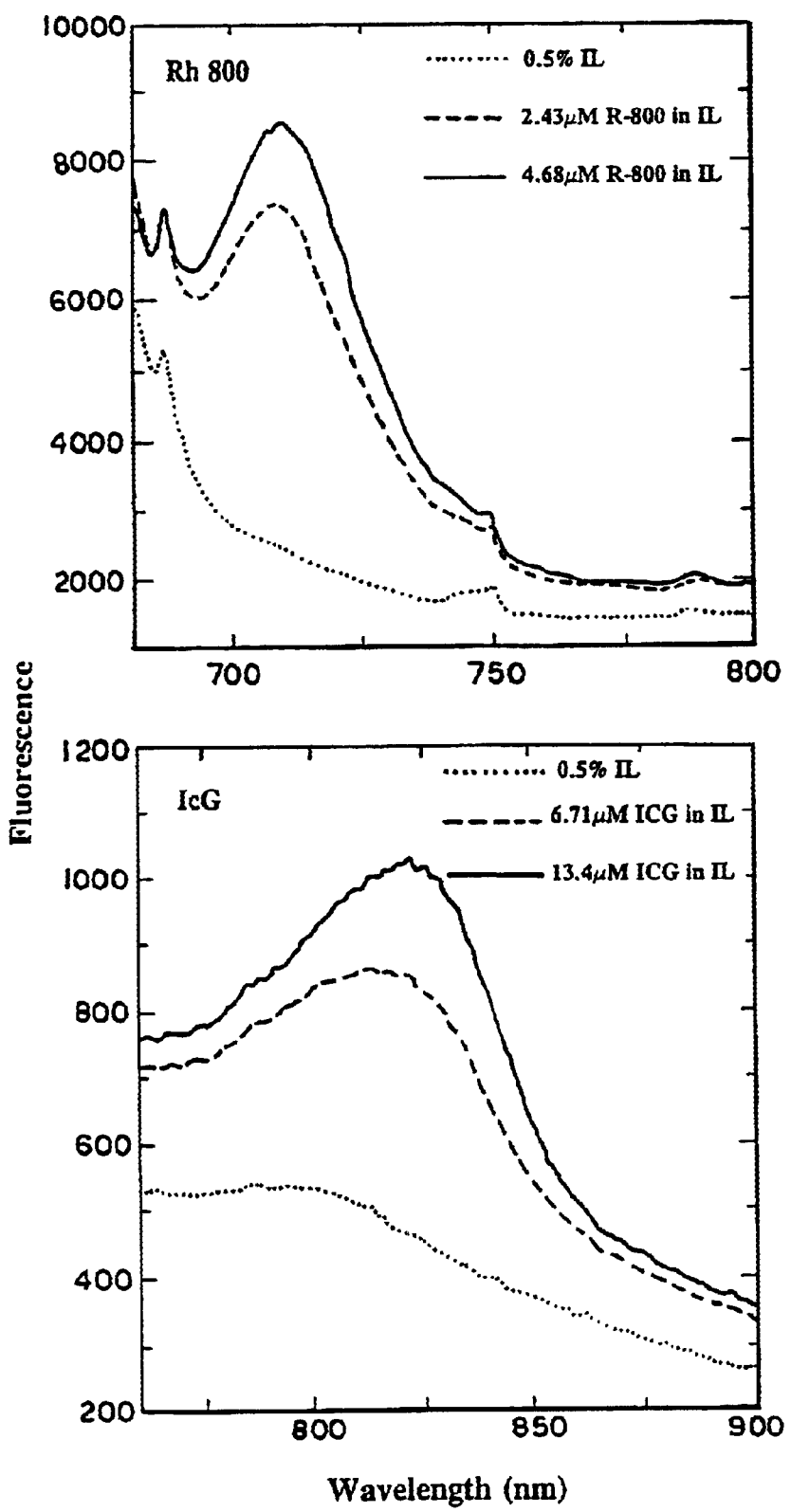
FIG. 14 provides two graphs showing emission spectra of Rh800 and IcG in 0.5% intralipid solution in a cuvette covered with chicken skin.
Figure 15:
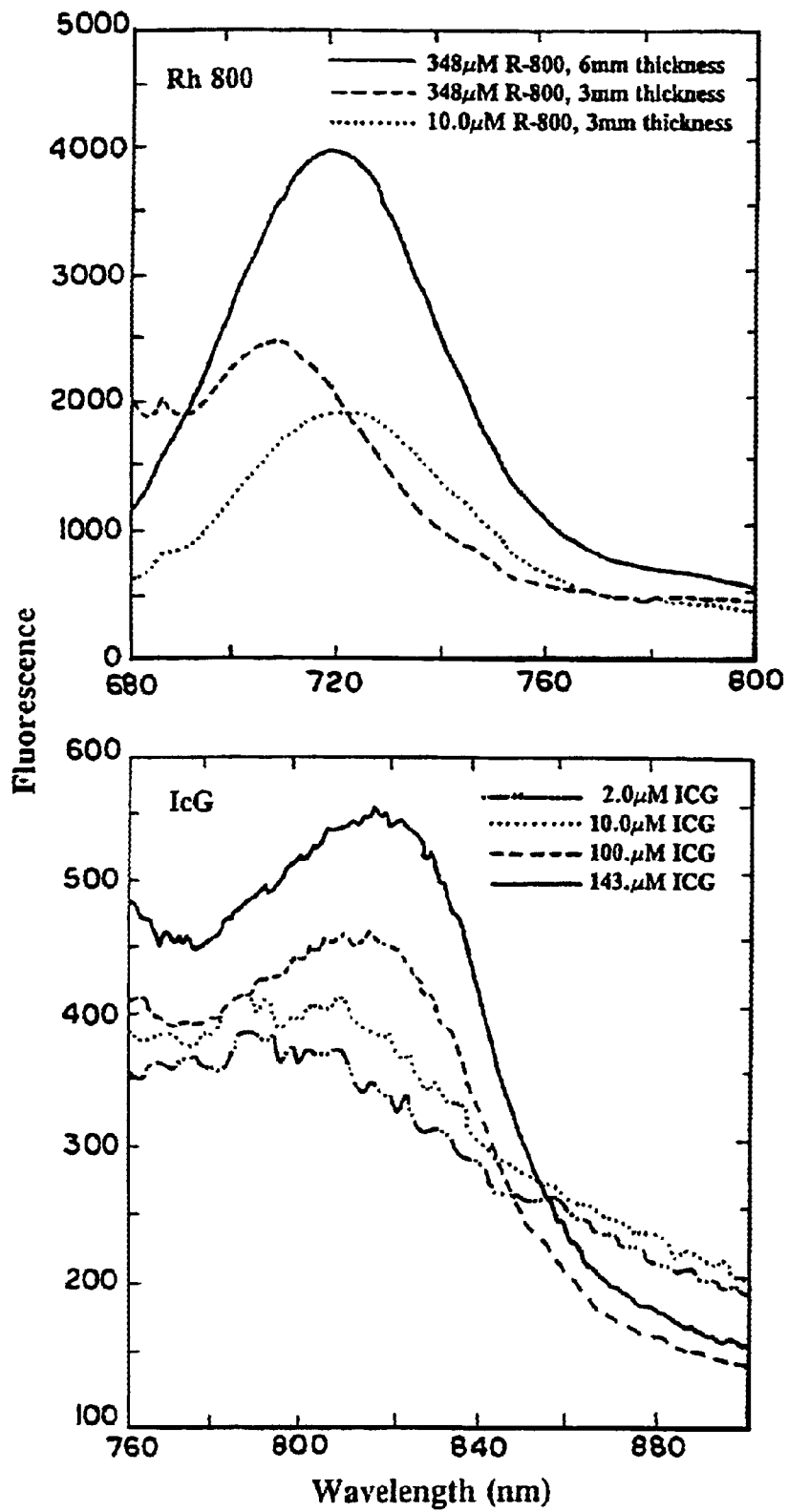
FIG. 15 provides two graphs showing emission from chicken tissue of Rh 800 (variable tissue thickness) and IcG (3 mm tissue thickness). Emission was observed through chicken skin over the muscle tissue.
Figure 16:
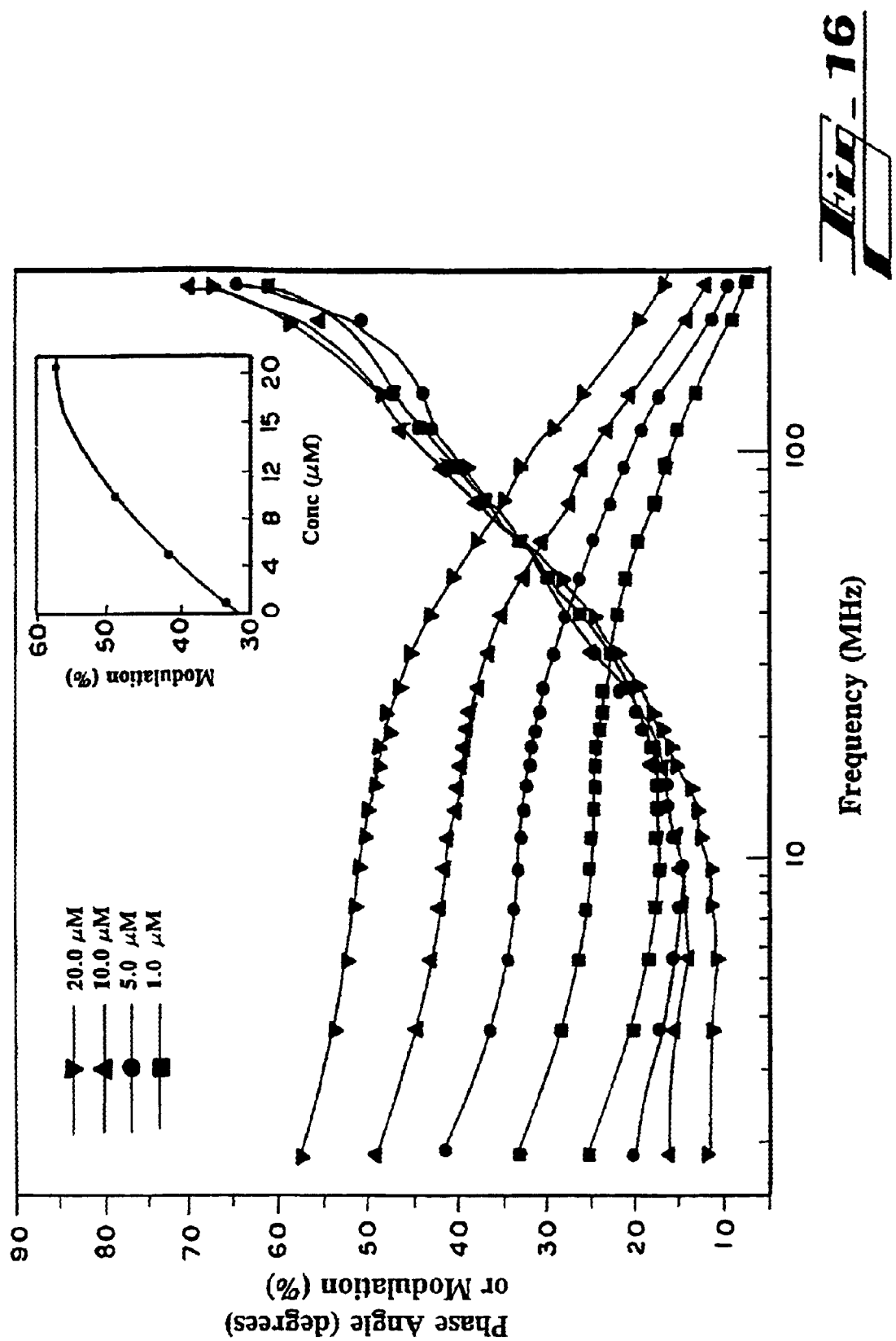
FIG. 16 provides a graph showing phase and modulation response for different concentrations of IcG in chicken tissue observed through PVA film containing ruthenium ligand complex. The inset shows the variation of the observed modulation with IcG concentration at 1.887 MHz.

The present invention can effectively monitor compliance by enabling measurement through skin and in tissues. We modeled this situation by placing chicken skin over the intralipid sample (FIG. 14). Emission from Rh800 and IcG could be detected, as seen by peaks at 710 and 820 nm, respectively. To obtain a still more realistic situation the intralipid was replaced by chicken muscle (FIG. 15). Peaks at 710 and 820 nm were still detectable. The emission spectra of the chicken muscle labeled with IcG is shown in FIG. 16. The low frequency modulation is seen to increase as the concentration of IcG increases. The low frequency concentration values can be used to estimate the IcG concentration in the tissues.

The above experiments and measurements show that fluorescent dyes can be detected non-invasively through the human skin using appropriate instrumentation. Concentrations of as low as 50 nM for Rh-800 (Table 11) and 250 nm for IcG (Table V) have been detected in this study reflecting the sensitivity of this technique.

Accordingly, by providing compositions comprising medications formulated with fluorescent dyes such as IcG, preferably in a time release formulations, therapeutic compliance can be determined non-invasively by the measurement of the modulation of the emission seen through the skin.

REFERENCES

1. Tan, K. K. (1995). Tuberculosis—Fighting a losing battle? *Singapore Med. J.* 36:209–211
2. Lordi, G. M., and Reichman, L. B. (1991). Treatment of tuberculosis, *American Family Physician,* 44:219–24
3. Waterhouse, R. M., Calzone, K. A., Mele, C., and Benner, D. E. (1993). Adherence to oral tamoxifen: A comparison of patient self-report, pill counts and microelectric monitoring, *J. Clin. Oncol.* 11:1189–1197
4. Cramer, J. A. (1995). Microelectric systems for monitoring and enhancing patient compliance with medication regimens, *Drugs* 46:321–327
5. Lee, J. Y., Wright, J. T., Wilkening, B., Smith, D., Norris, K., Berhnard, S., Green, P. G., and Kusek, J. W. (1996). Assessing medication adherence by pill count and electronic monitoring in the African American Study of kidney disease and hypertension (AAKS) pilot study, *Am. J. Hypertens.* 9(8):719–725
6. Mallion, J. M., de Gaudemaris, R., Termel, F., Siche, J. P., and Baguet, J. P., (1998). Compliance, electronic monitoring and antihypertensive drugs, *J. Hypertens. Suppl.* 16(1): S75–S79
7. Wilson, B. C., Patterson, M. S., and Bums, D. M., (1986). Effect of photosensitzer concentration in tissue on the penetration depth of photoactivating light, *Laser Med. Sci.* 1:235–244
8. Lakowicz, J. R., and Maliwal, B. P. (1985). Construction and performance of a variable-frequency phase-modulation fluorometer, *Biophys. Chem.* 21:61–78
9. Lakowicz, J. R., Laczko, G., and Gryczynski, I. (1986). A 2 GHz frequency-domain fluorometer, *Rev. Sci. Instrum.* 57: 2499–2506
10. Laczko, G., Lakowicz, J. R., Gryczynski, I., Gryczynski, Z., and Malak, H. (1990). A 10 GHz frequency-domain fluorometer, *Rev. Sci. Instrum.* 61:2331–2337
11. Lakowicz, J. R., and Gryczynski, I. (1991). Frequency-domain fluorescence spectroscopy in *Topics in Fluorescence spectroscopy, Vol* 1: *Techniques* (J. R. Lakowicz, J. R., Ed.), Plenum Press, New York, pp. 293–335
12. Berndt, K., Duerr, H., and Palme, D. (1982). Picosecond phase fluorometry by mode-locked CW lasers, *Opt. Commun.* 42:419–422
13. Gratton, E., and Lopez-Delgado, R. (1980). Measuring fluorescense decay times by phase-shift and modulation techniques using the high harmonic content of pulsed light sources, *Nuovo Cimento.* B56:110–124
14. Gratton, E., James, D. M., Rosato, N., and Weber, G. (1984). Multifrequency cross-correlation phase fluorometer using synchrotron radiation, *Rev. Sci. Instrum.* 55:486–494
15. Sacksteder, K., Lee, M., Demas, J. N., and DeGraff, B. A. (1983). Long lived, highly luminescent rhenium(I) complexes as molecular probes: Intra- and intermolecular excited state interactions, *J. Am. Chem. Soc.* 115:8230–8238
16. Demas, J. N., and DeGraff, B. A. (1994). Design and applications of highly luminescent transition metal complexes in *Topics in Fluorescence Spectroscopy, Vol.* 4.: *Probe Design and Chemical Sensing* (J. R. Lackowicz, Ed.), Plenum Press, New York, pp. 71–107
17. Murphy, C. J., Nair, R. B., Keller, C. E., Teng, E. S., and Pollard, C. (1997). Dipyridophenazine complexes of Ru(II): Versatile optical sensors for small and large molecules, *SPIE Proc.* 2980:473–478
18. Nair, R. B., Cullum, B. M., and Murphy, C. J. (1997). Optical properties of $[Ru(phen)_2dppz]^{2+}$ as a function of nonaqueous environment, *Inorg. Chem.* 36:962–965
19. Ott, P. T., Keiding, S., Johnsen, A. H., and Bass, L. (1994). Hepatic removal of two fractions of indocyanine green after bolus injection in anesthetized pigs, *Am.J. Physiol.* 266(6): G1108–G1112
20. Bollinger, A., Saesseli, B., Hollmann, U., and Franzeck, J. K. (1991). Intravital detection of skin capillary aneurysms by videomicroscopy with indocyanine green in patients with progressive systematic sclerosis and related disorders, *Circulation* pp. 546–551
21. Mordon, S., Desmettre, T., Devoisselle, J-M., and Mitchell, V. (1997). Selective laser photocoagulation of blood vessels in a hamster skin flap model using a specific ICG formulation, *Lasers in Surg. and Med.* 21:365–373
22. Nakayama, M., Kanaya, N., Fujita, S., and Namiki, A. (1993). Effects of ephedrine on indocyanine green clearance during spinal anesthesia: evaluation by the finger piece method, *Anesth. Analg.* 77:947–949
23. Henschen, S., Busse, M. W., Zisowksy, S., and Panning, B. (1993). Determination of plasma volume and total blood volume using indocyanine green: A short review, *J. Med.* 24:10–27
24. Schomacker, K. T., Torri, A., Sandison, D. R., Sheridan, R. L. and Nishioka, N. S. (1997). Biodistribution of indocyanine green in a porcine burn model: Light and fluorescence microscopy, *J. Trauma Injury, Infection,* 43:813–819
25. Sheridan, R. L., Schomacker, K. T., Lucchina, L. C., Hurley, J., Yin, L. M., Tompkins, R. G., Jerath, M., Torri, A., Greaves, K. W., Bua, D. P., and Nishioha, N. S. (1995). Burn depth estimation by use of indocyanine green fluorescence initial human trial, *J. Burn Care Rehabil.* 16(6):602–604
26. Hollins, B., Noe, B., and Henderson, J. M. (1987). Fluorometric determination of indocyanine green in plasma, *Clin. Chem.* 33(6):765–768
27. Dorshow, R. B., Bugaj, J. E., Burleigh, B. D., Duncan, J. R., Johnson, M. A., and Jones, W. B. (1998). Noninvasive fluorescence detection of hepatic and renal function, *J. Biomed. Optics* 3(3):340–345
28. Kanda, M., and Niwa, S. (1992). Development of a noninvasive monitoring instrument for serum indocyanine green dye concentration, *Appl. Optics.* 31(31):6668–6675
29. Mordon, S., Deviosselle, J-M., Soulie-Begu, S., and Desmettre, T. (1998). Indocyanine green: Physiochemical factors affecting its fluorescence in vivo, *Microvascular* 55:146–152
30. Zhou, J. F., Chin, M. P., and Schafer, S. A. (1994). Aggregation and degradation of indocyanine green, *SPIE Proc.* 2128:495–508
31. Landsman, M. L. J., Kwant, G., Mook, G. A., and Zijlstra, W. G. (1976). Light-absorbing properties, stability, and spectral stabilization of indocyanine green. *J. Appl. Phy.* 40(4): 575–583
32. Devoisselle, J. M., Soulie, S., Mordon, S., Desmettere, T., and Maillols, H. (1997). Fluorescence properties of indocyanine green—Part 1: In-vitro study related to in vivo behavior, *SPIE Proc.* 2980:453–460
33. Devoisselle, J. M., Soulie, S., Maillols, H., Desmettere, T., and Mordon, S. (1997). Fluorescence properties of indocyanine green—Part 2: In-vitro study related to in vivo behavior, *SPIE Proc.* 2980:293–302
34. van den Biesen, P. R., Jongsma, F. H., Tangelder, G. J., and Slaaf, D. W. (1995). Yield of fluorescence from indocyanine green in plasma and flowing blood. *Annals of Biomed. Eng.* 23:475–481
35. Fantini, S., Franceschini, M. A., Fishkin, J. B., Barbieri, B., and Gratton, E. (1994). Quantative determination of the absorption spectra of chromophores in strongly scattering media: a light-emitting diode based technique. *Appl. Optics* 33(22):5204–5213
36. Sipior, J., Carter, G. M., Lakowicz, J. R. and Rao, G. (1996). Single quantum well light emitting diodes demonstrated as excitation sources for nanosecond phase-modulation fluorescence lifetime measurements. *Rev. Scie. Instrum.* 67(11):3795–3798
37. Sipior, J., Carter, G. M., Lakowicz, J. R. and Rao, G. (1997). Blue-light-emitting diode demonstrated as an ultraviolet excitation source for nanosecond phase-modulation fluorescence lifetime measurements. *Rev. Sci. Instrum.* 68(7):2666–2670

We claim:

1. A method for monitoring drug therapy compliance by a human or animal patient, comprising contacting the patient with a transdermal detection device capable of receiving a signal from a labeled pill administered to the patient, wherein transdermal detection of the signal indicates that the patient has received a predetermined amount of the labeled pill.

2. The method of claim 1, wherein the pill is labeled with a fluorescent label, and the transdermal detection device detects a fluorescent signal emitted from the fluorescent label in the patient.

3. The method of claim 2, wherein the fluorescent label comprises one or more compounds selected from the group consisting of fluorescein, indocyanin green, and rhodamine B.

4. The method of claim 1, wherein the labeled pill comprises a drug selected from the group consisting of an antimicrobial agent, antibiotic, antiviral, antidepressant, β-lactam antibiotic, aminoglycoside, macrolide, lincomycin, clindamycin, tetracycline, quinolone, polypeptide, sulfonamide, trimethoprim, sulfamethoxazole, growth factor, lipid, neurotransmitter, vitamin, and mineral.

5. The method of claim 1, wherein the pill is administered to treat a disease or disorder selected from the group consisting of infectious disease, immunodeficiency disease, cardiovascular disorder, pulmonary disorder, gastrointestinal disorder, hepatic disorder, biliary disorder, endocrine disorder, cancer, musculoskeletal disorder, connective tissue disorder, neurologic disorder, psychiatric disorder and genitourinary disorder.

6. The method of claim 5, wherein the infectious disease comprises mycobacterial disease.

7. The method of claim 6, wherein the mycobacterial disease is caused by infection with a Mycobacterial strain selected from the group consisting of *Mycobacterium tuberculosis, Mycobacterium avium-intracellular, Mycobacterium kansasii, Mycobacterium frotiutun, Mycobacterium chelonae,* and *Mycobacterium leprae.*

8. The method of claim 5, wherein the infectious disease is tuberculosis.

9. The method of claim 5, wherein the psychiatric disorder is a substance abuse disorder.

10. A method for monitoring drug therapy compliance in a patient being treated for substance abuse comprising contacting the patient with a transdermal detection device capable of receiving a signal from a labeled pill administered to the patient, wherein transdermal detection of the signal indicates that the patient has received a predetermined amount of the labeled drug.

* * * * *

UNITED STATES PATENT AND TRADEMARK OFFICE
CERTIFICATE OF CORRECTION

| | | |
|---|---|---|
| PATENT NO. | : 6,663,846 B1 | Page 1 of 1 |
| APPLICATION NO. | : 09/468718 | |
| DATED | : December 16, 2003 | |
| INVENTOR(S) | : Candace McCombs et al. | |

It is certified that error appears in the above-identified patent and that said Letters Patent is hereby corrected as shown below:

Column 1, line 11, insert the following statement:

-- GOVERNMENT RIGHTS

This invention was made with government support under Grant Number RR008119 awarded by the National Institutes of Health. The government has certain rights in the invention. --

Signed and Sealed this

Twenty-seventh Day of November, 2012

David J. Kappos
*Director of the United States Patent and Trademark Office*